United States Patent
Tamura et al.

(10) Patent No.: US 10,849,487 B2
(45) Date of Patent: Dec. 1, 2020

(54) ILLUMINATION UNIT AND ENDOSCOPE SYSTEM

(71) Applicant: OLYMPUS CORPORATION, Tokyo (JP)

(72) Inventors: Kazuaki Tamura, Hachioji (JP); Satoshi Ohara, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/690,247

(22) Filed: Nov. 21, 2019

(65) Prior Publication Data
US 2020/0085288 A1 Mar. 19, 2020

Related U.S. Application Data

(63) Continuation of application No. PCT/JP2017/019268, filed on May 23, 2017.

(51) Int. Cl.
*F21V 9/30* (2018.01)
*A61B 1/06* (2006.01)
(Continued)

(52) U.S. Cl.
CPC .............. *A61B 1/0653* (2013.01); *A61B 1/07* (2013.01); *F21V 9/30* (2018.02); *G02B 6/0008* (2013.01)

(58) Field of Classification Search
CPC ........... G02B 6/0008; G02B 6/00; G02B 6/26
See application file for complete search history.

(56) References Cited

U.S. PATENT DOCUMENTS 5,989,185 A * 11/1999 Miyazaki ........... A61B 1/00096
348/E7.085
10,441,156 B2 * 10/2019 Peterson ................. A61F 9/007
(Continued)

FOREIGN PATENT DOCUMENTS

JP 2007-188059 A 7/2007
JP 2011-123368 A 6/2011
(Continued)

OTHER PUBLICATIONS

English translation of International Preliminary Report on Patentability dated Dec. 5, 2019, together with the Written Opinion received in related International Application No. PCT/JP2017/019268.

(Continued)

*Primary Examiner* — Evan P Dzierzynski
(74) *Attorney, Agent, or Firm* — Scully, Scott, Murphy & Presser, P.C.

(57) ABSTRACT

An illumination unit includes a light guide to guide primary light, a conversion member to convert the primary light into secondary light, and a holder holding an exit end of the light guide and the conversion member. The holder includes an entrance portion that the primary light enters, an exit portion to emit illumination light including the secondary light, and a fixing portion fixing the conversion member between the entrance portion and the exit portion in a direction of a central axis of the primary light. The fixing portion is arranged in a planar region perpendicular to the central axis of the primary light and on an inner peripheral face of the holder. The conversion member is in contact with the fixing portion.

20 Claims, 19 Drawing Sheets

(51) Int. Cl.
*A61B 1/07* (2006.01)
*F21V 8/00* (2006.01)

(56) References Cited

U.S. PATENT DOCUMENTS

| | | | |
|---|---|---|---|
| 2010/0080016 A1* | 4/2010 | Fukui | G02B 6/32 362/574 |
| 2011/0090679 A1* | 4/2011 | Geuder | A61B 1/0669 362/183 |
| 2012/0014115 A1* | 1/2012 | Park | G02B 19/0014 362/311.02 |
| 2014/0022810 A1 | 1/2014 | Ito et al. | |
| 2017/0014022 A1 | 1/2017 | Tamura et al. | |

FOREIGN PATENT DOCUMENTS

| | | |
|---|---|---|
| JP | 4737611 B2 | 8/2011 |
| JP | 2012-185318 A | 9/2012 |
| JP | 2014-174192 A | 9/2014 |

OTHER PUBLICATIONS

International Search Report dated Aug. 15, 2017 issued in PCT/JP2017/019268.
English Abstract of JP 2007121502A, dated May 17, 2007.

* cited by examiner

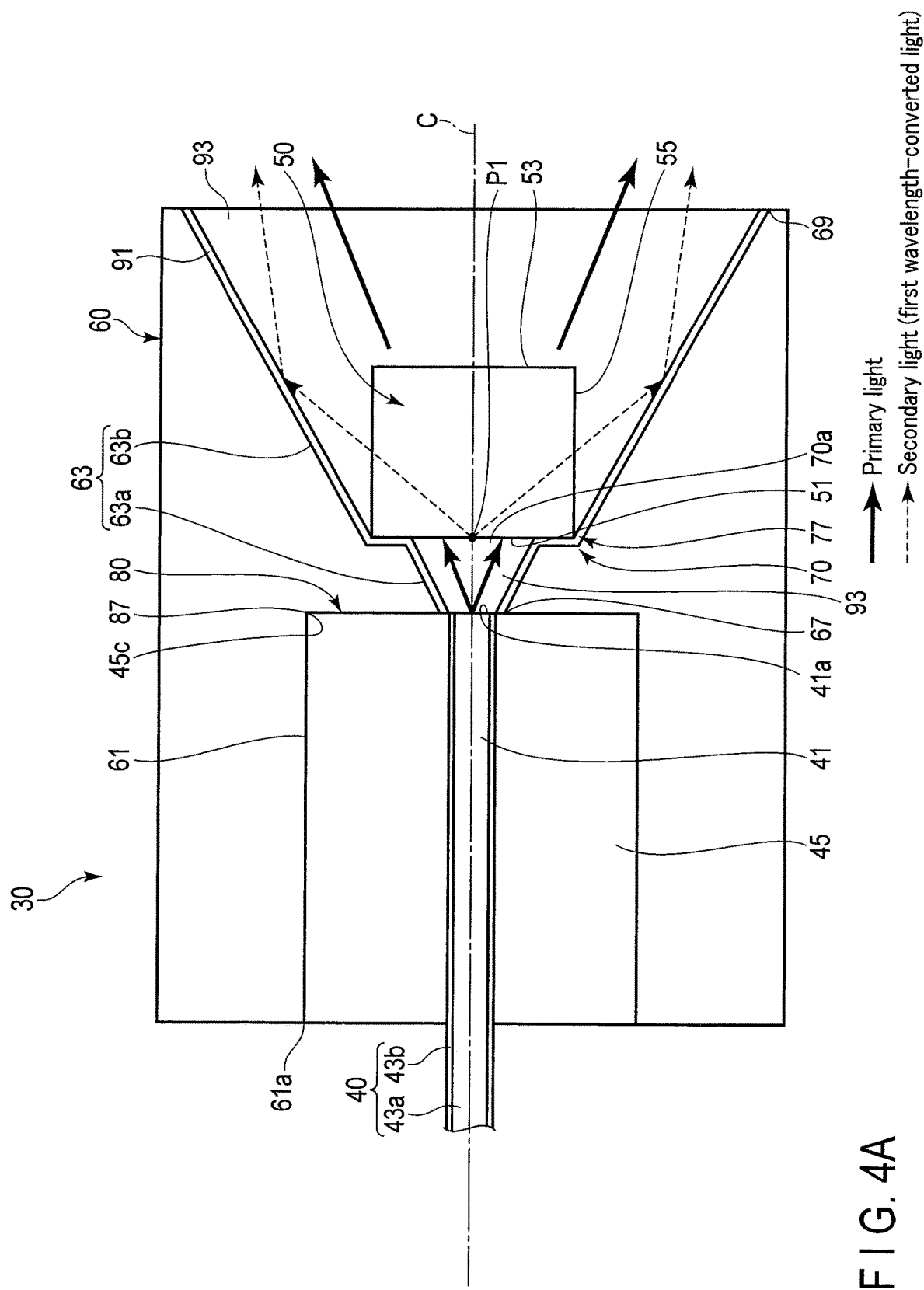
F I G. 4A

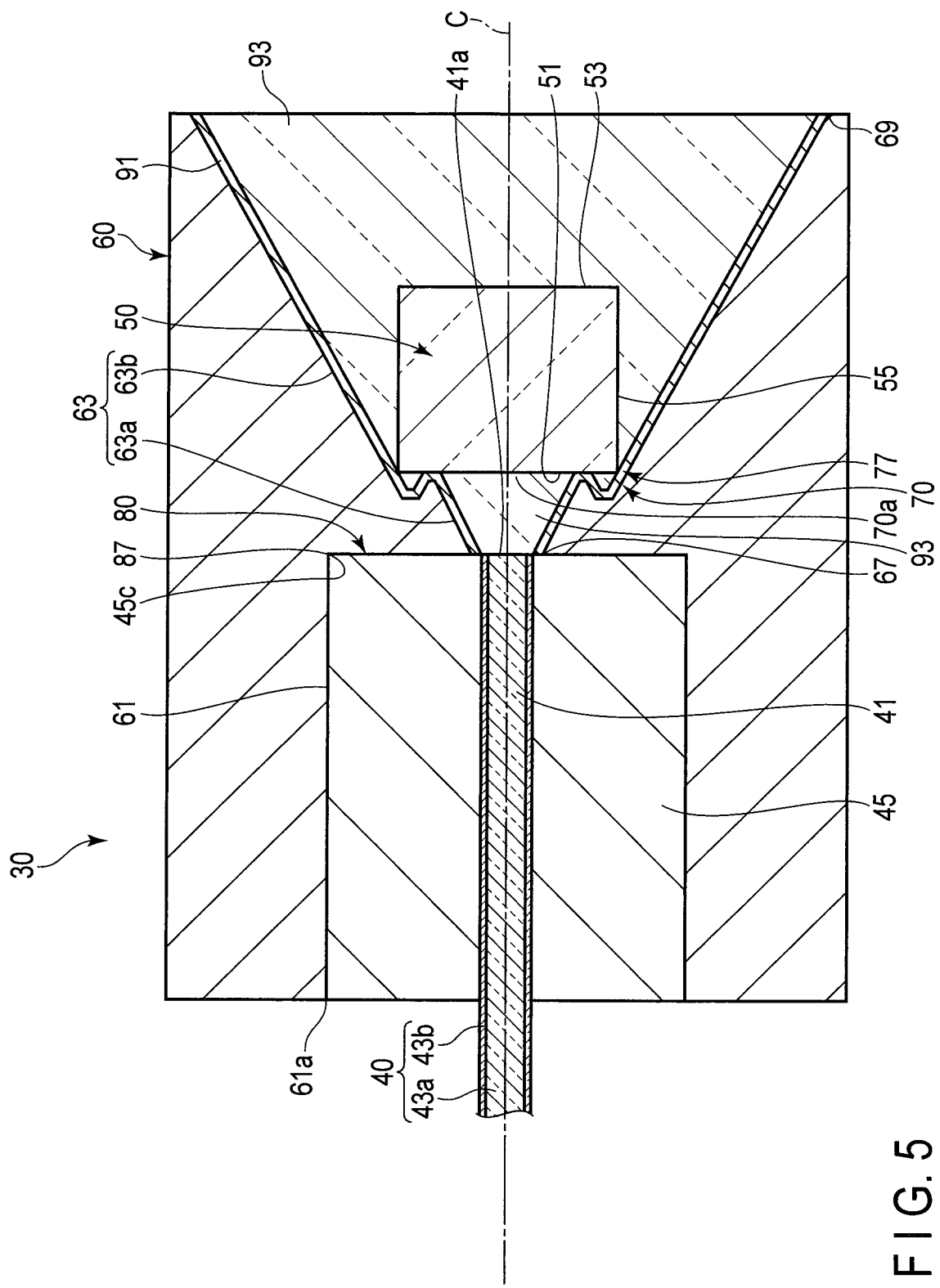
F I G. 5

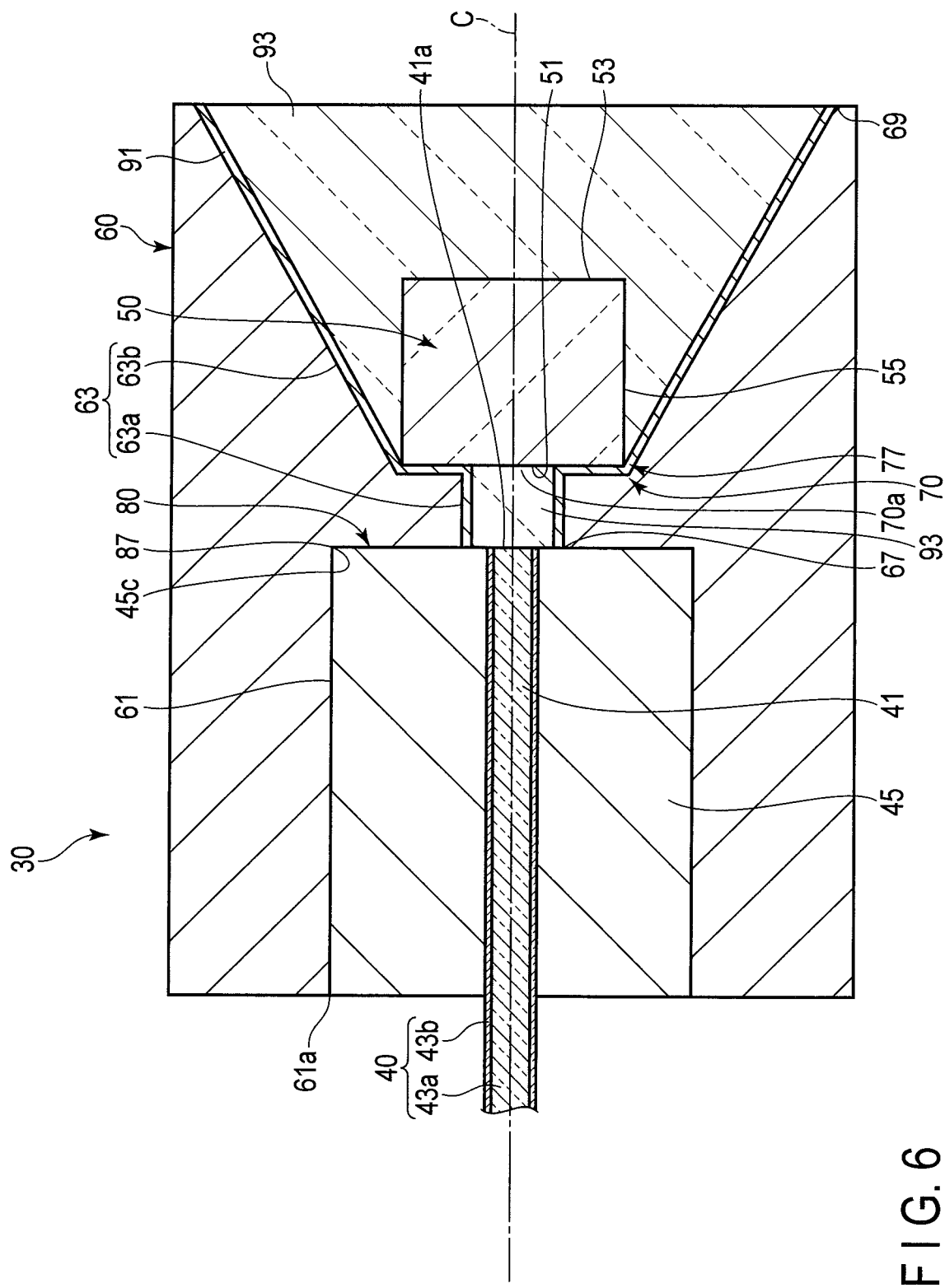
F I G. 6

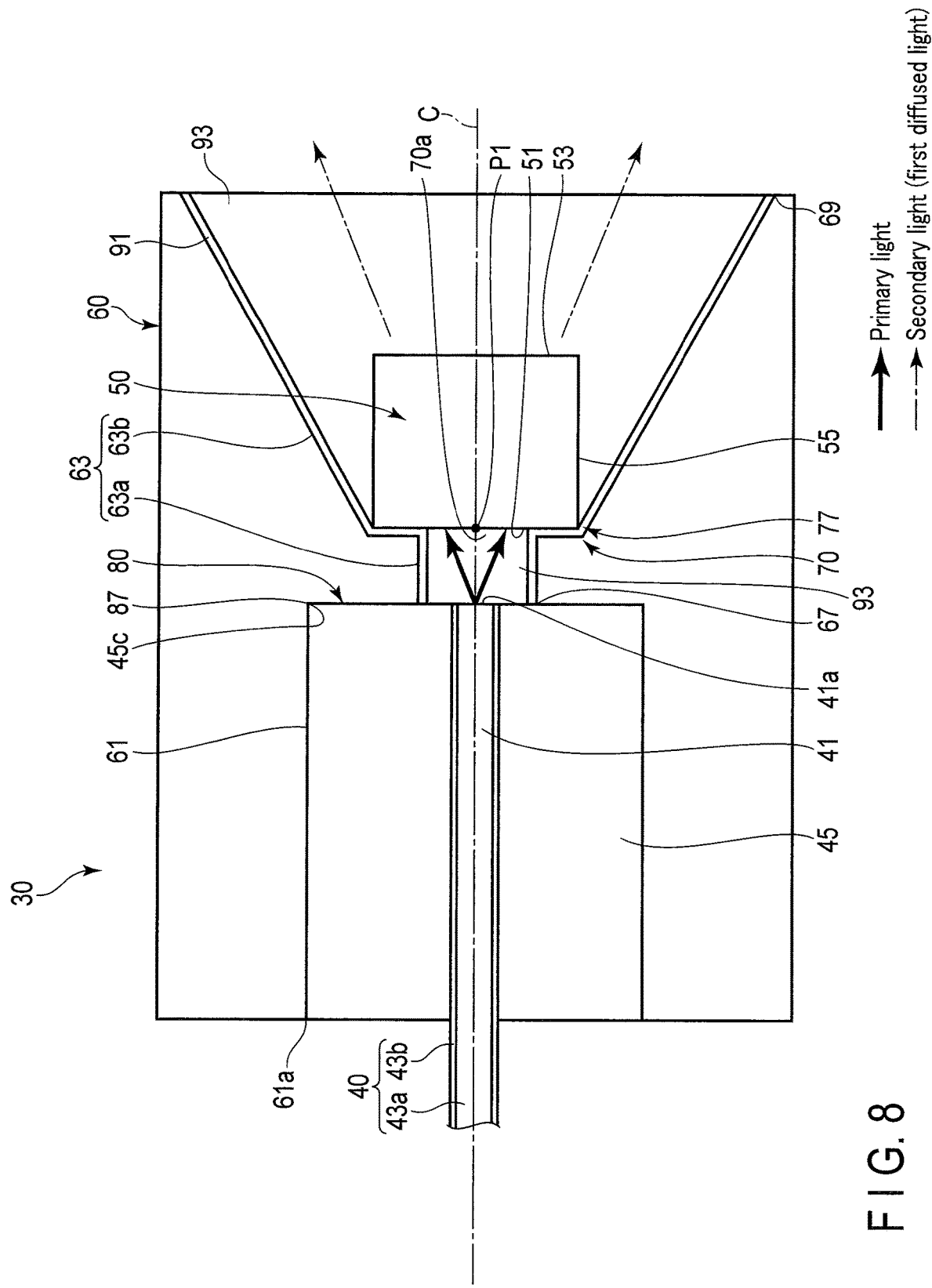
F I G. 8

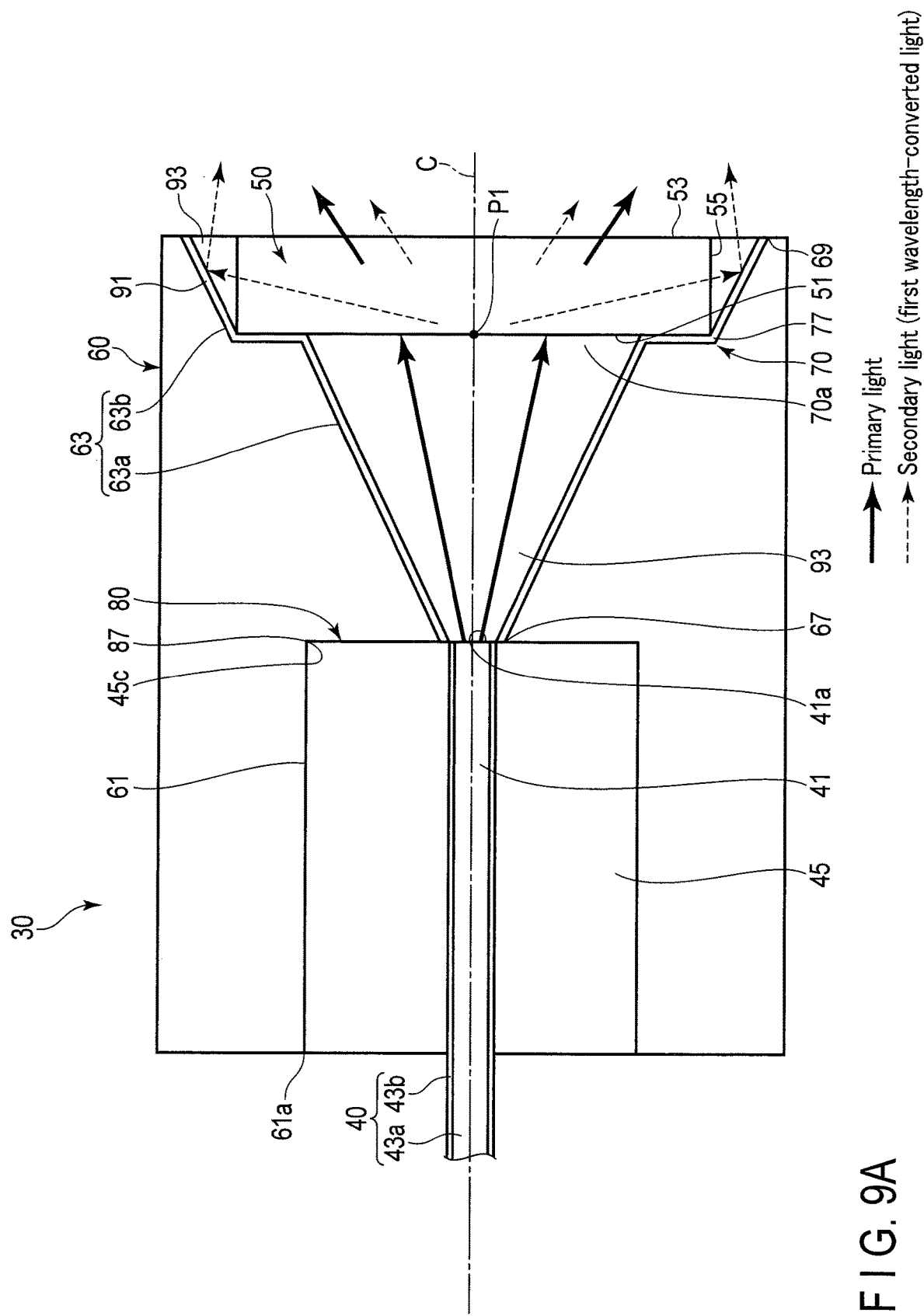
F I G. 9A

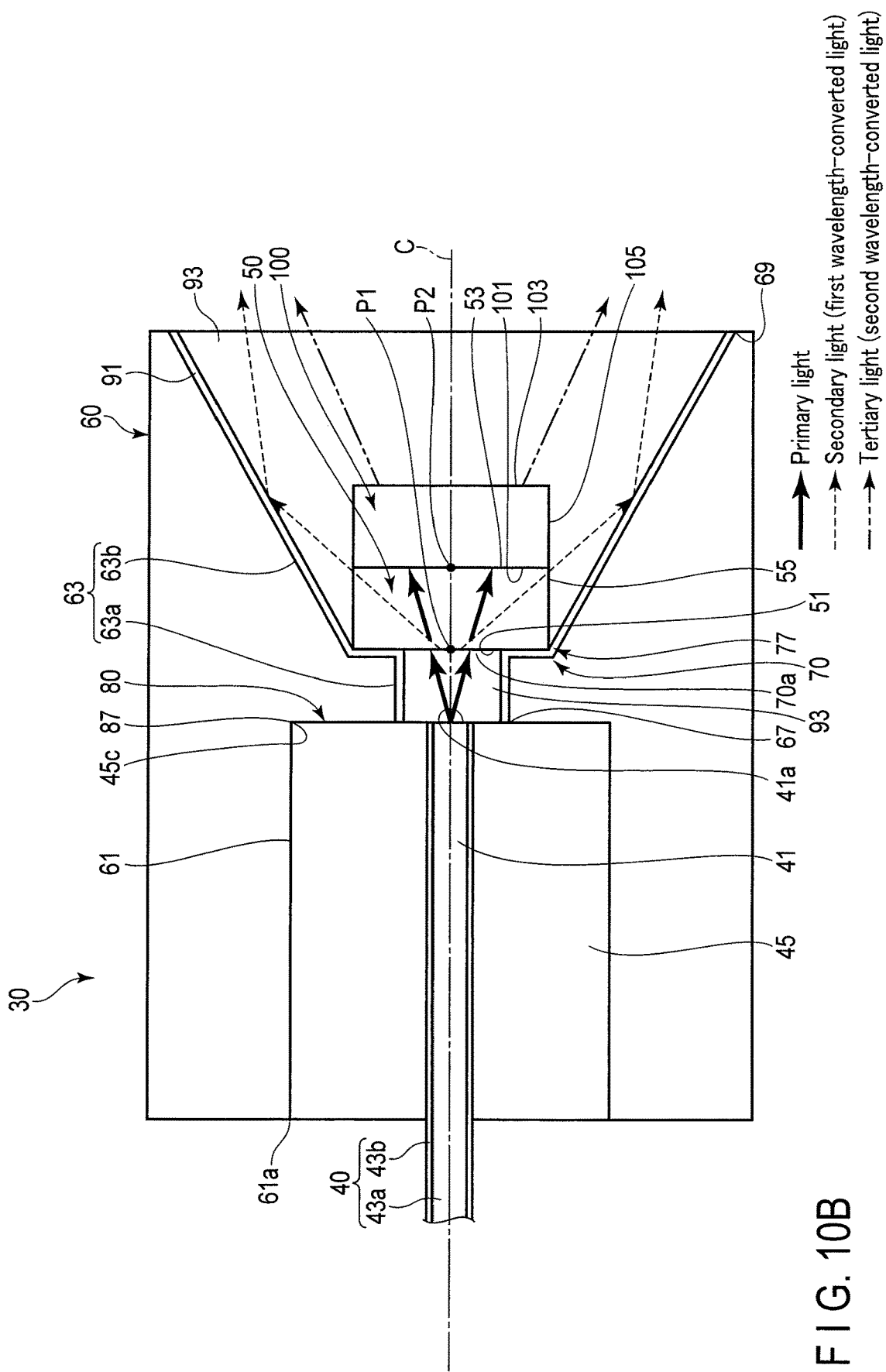
F I G. 10B

ILLUMINATION UNIT AND ENDOSCOPE SYSTEM

CROSS-REFERENCE TO RELATED APPLICATIONS

This application is a Continuation Application of PCT Application No. PCT/JP2017/019268, filed May 23, 2017, the entire contents of which are incorporated herein by reference.

BACKGROUND OF THE INVENTION

1. Field of the Invention

The present invention relates to an illumination unit and an endoscope system.

2. Description of the Related Art

A fiber light source is proposed in which light emitted from a compact solid-state light source is wavelength-converted by a wavelength conversion member arranged at the exit end of an optical fiber and in which a light irradiation pattern and color are changed as desired.

For example, Japanese Patent No. 4737611 discloses a light emitting device having an optical fiber and an optical component attached to the exit end portion of the optical fiber. The optical component includes a ferrule attached to the end portion of the optical fiber, a reflector to which the ferrule is attached, and a phosphor that is arranged on the reflector and located forward of the optical fiber and that is configured to convert incident light to fluorescence. The optical component has a reflection member arranged between the end portion and the phosphor. The reflection member and the inner peripheral face of the reflector arranged around the phosphor reflect the fluorescence. Thereby, an optical component having high extraction efficiency of fluorescence used as illumination light is realized.

BRIEF SUMMARY OF THE INVENTION

An illumination unit according to the present invention includes: a light guide configured to guide primary light and having an exit end configured to emit the primary light; a first light conversion member that is irradiated with the primary light emitted from the exit end and that is configured to convert at least part of the primary light into secondary light having optical characteristics different from optical characteristics of the primary light; and a holder holding the exit end and the first light conversion member. The holder includes: a holder entrance portion that the primary light enters; a holder exit portion configured to emit illumination light including at least the secondary light and having a diameter larger than a diameter of the first light conversion member; and a first fixing portion that is arranged between the holder entrance portion and the holder exit portion in a direction of a central axis of the primary light traveling from the holder entrance portion to the first light conversion member and that fixes the first light conversion member in the direction of the central axis so that the first light conversion member is arranged between the holder entrance portion and the holder exit portion. The first fixing portion is arranged in a planar region substantially perpendicular to the central axis of the primary light and on an inner peripheral face of the holder. The first light conversion member is in contact with at least part of the first fixing portion.

An endoscope system according to the present invention includes an endoscope and the above mentioned illumination unit that is located in the endoscope.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4A is a diagram schematically showing how primary light and secondary light travel in the illumination unit shown in FIG. 2A.

FIG. 5 is a diagram showing that the first fixing portion has a rough face.

FIG. 6 is a diagram schematically showing an illumination unit according to modification 1 of the first embodiment.

FIG. 8 is a diagram schematically showing how primary light and secondary light travel in an illumination unit according to modification 3 of the first embodiment.

FIG. 9A is a diagram schematically showing how primary light and secondary light travel in an illumination unit according to modification 4 of the first embodiment.

FIG. 10B is a diagram schematically showing how primary light, secondary light and tertiary light travel in the illumination unit shown in FIG. 10A.

DETAILED DESCRIPTION OF THE INVENTION

Embodiments of the present invention will be described with reference to the accompanying drawings. Note that in some of the drawings, some of the members are not shown for clarity of illustration.

The central axis of primary light traveling from a holder entrance portion 67 to a first light conversion member 50 will be referred to as a central axis C. The central axis C direction indicates, for example, a direction from the holder entrance portion 67 toward the first light conversion member 50, and is, for example, a direction from the left side to the right side in FIG. 2A. In the central axis C direction, the light source unit 20 side will be referred to as the rear, and the holder exit portion 69 side will be referred to as the front.

Figure 3A:
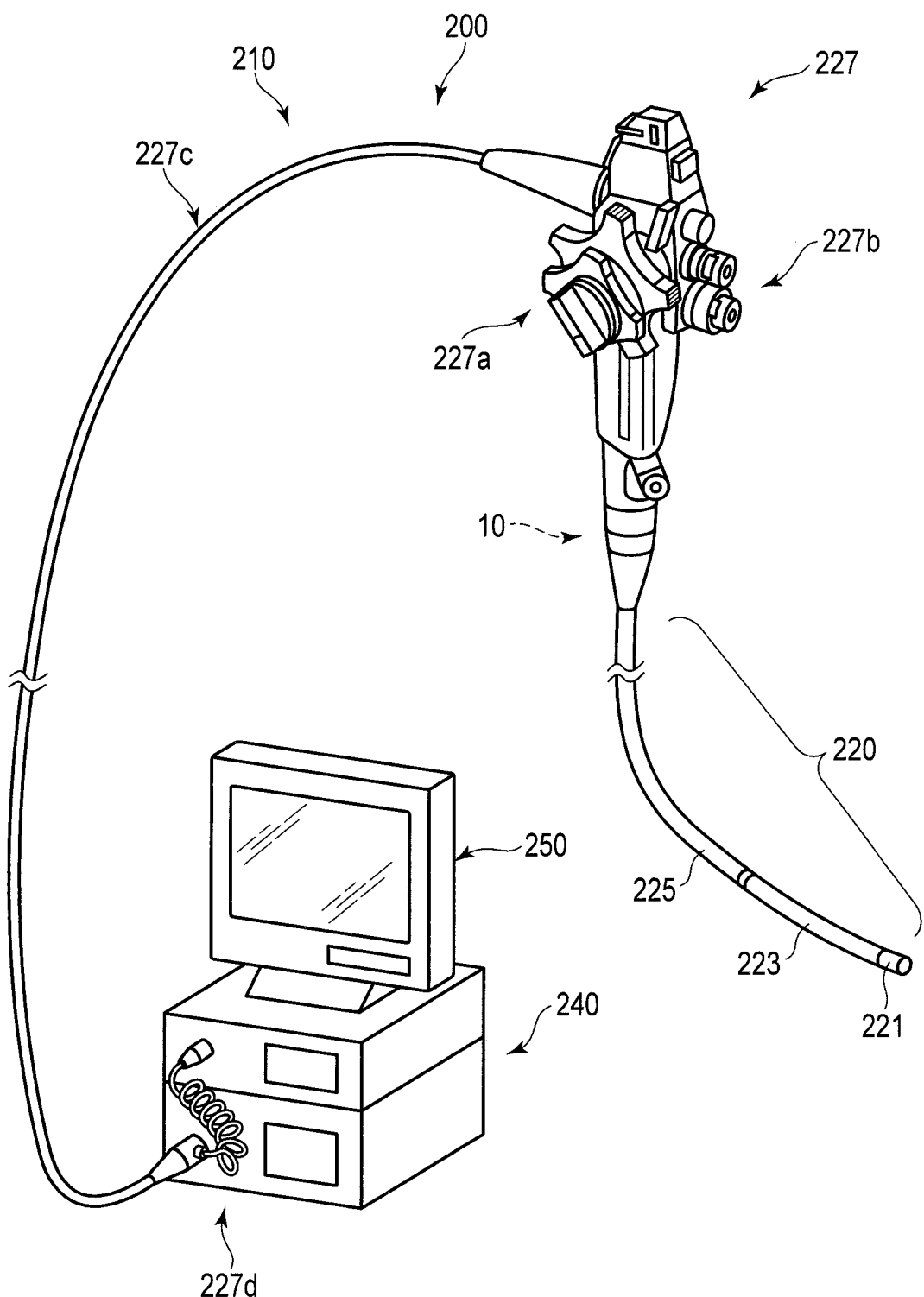
FIG. 3A is a schematic view of an endoscope system installed with the illumination device shown in FIG. 1A.

The illumination device 10 shown in FIG. 1 will be described as, for example, an endoscope illumination device installed in an endoscope 210 of an endoscope system 200 shown in, for example, FIG. 3A. The endoscope 210 is an example of a small precision device. Examples of the precision devices include a microscope and an illumination probe, in addition to the endoscope 210. The illumination device 10 may function as, for example, a device used alone.

First Embodiment

A description will now be given of the first embodiment of the present invention.

Figure 1:
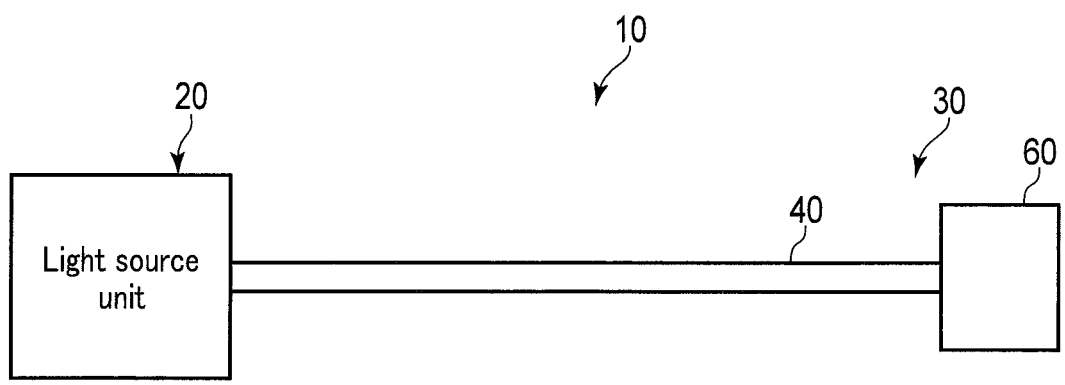
FIG. 1 is a schematic view of an illumination device having an illumination unit according to the first embodiment of the present invention.

As shown in FIG. 1, the illumination device 10 includes a light source unit 20 and an illumination unit 30.

The light source unit 20 includes a light source 21 (see FIG. 3B) configured to emit the primary light having a wavelength in the visible light region toward the illumination unit 30. For example, the light source 21 includes a laser diode configured to emit laser light as the primary light. For example, the color of the laser beam is blue, and the center wavelength of the laser beam is 445 nm.

Figure 2A:
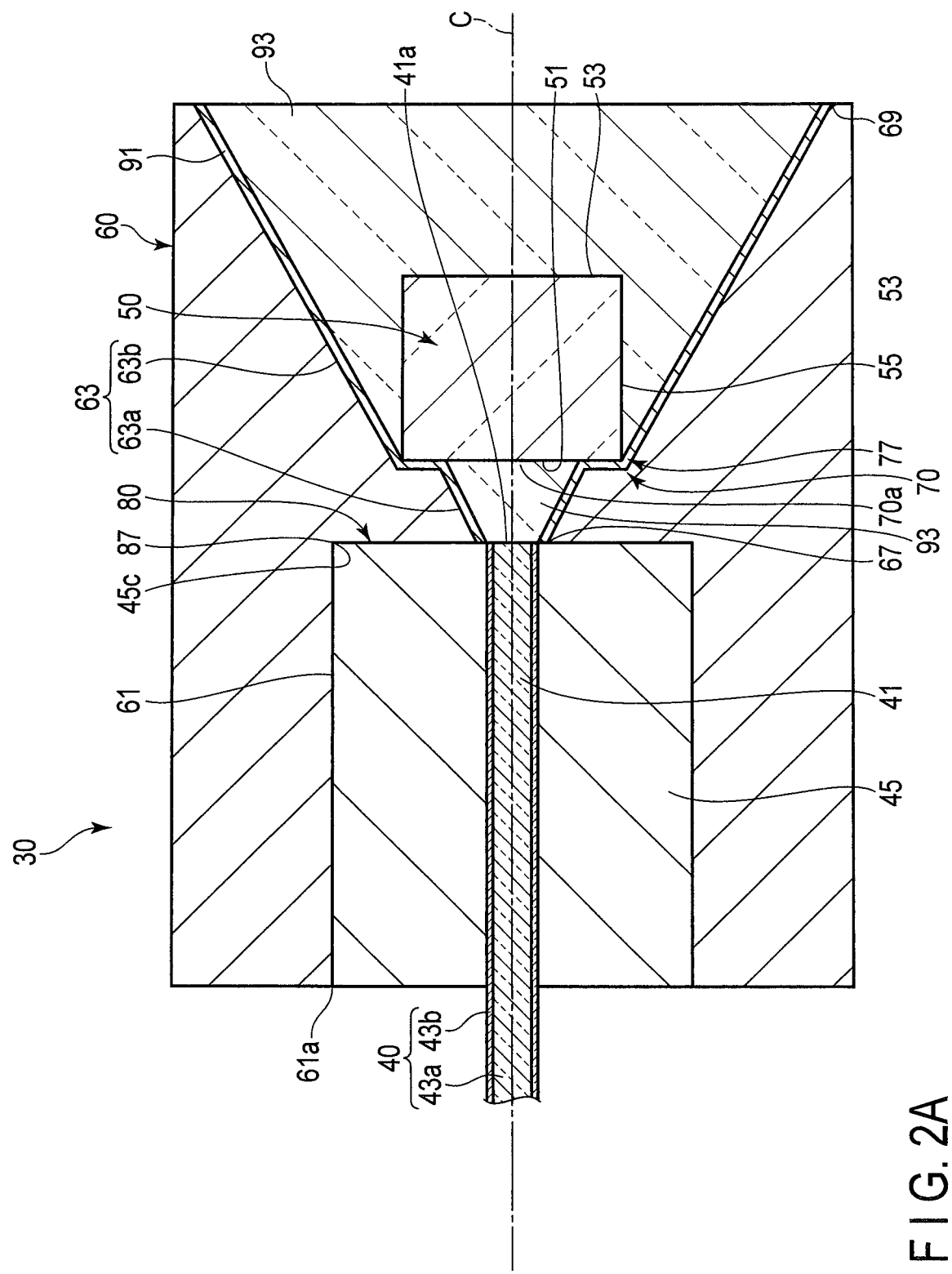
FIG. 2A is a diagram schematically showing the illumination unit shown in FIG. 1.

As shown in FIGS. 1 and 2A, the illumination unit 30 includes a light guide 40 configured to guide the primary light. The light guide 40 has an exit end 41 including an exit end face 41a configured to emit the primary light. The illumination unit 30 includes a first light conversion member 50 that is irradiated with the primary light emitted from the exit end face 41a and that is configured to convert at least part of the primary light into secondary light having optical characteristics different from optical characteristics of the primary light, and also includes a holder 60 holding the exit end 41 of the light guide 40 and the first light conversion member 50.

The light guide 40 is optically connected to the light source unit 20 and the first light conversion member 50, and guides the primary light emitted from the light source unit 20 to the first light conversion member 50. The light guide 40 may be detachable from the light source unit 20.

Since laser light is used as the primary light, the light guide 40 is, for example, a single-line optical fiber, and the optical fiber is, for example, a multi-mode optical fiber. The light guide 40 may be a bundle fiber.

The light guide 40 includes a core 43a arranged in the center of the light guide 40, and a cladding 43b arranged on the outer periphery of the core 43a and covering entire periphery of the core 43a. The refractive index of the core 43a is higher than the refractive index of the cladding 43b. Owing to the difference between the refractive index of the core 43a and the refractive index of the cladding 43b, the cladding 43b has a function of confining the primary light to the core 43a, and the primary light is totally reflected by the cladding 43b and is efficiently guided by the core 43a.

For example, the core 43a has a diameter of 50 μm and a numerical aperture (NA) of 0.2.

For example, the material of the optical fiber is quartz glass, plastic or resin.

Although not shown, the light guide 40 may have a jacket that is arranged on the outer periphery of the cladding 43b and covers the entire periphery of the cladding 43b. As the jacket, for example, a resin such as nylon, acrylic, polyimide, or ETFE is used. The jacket improves the mechanical strength of the light guide 40, such as tensile resistance and bending resistance.

The light guide 40 has an exit end face 41a that is perpendicular to the central axis of the light guide 40. The exit end face 41a is a flat face configured to emit the primary light to the first light conversion member 50. The exit end face 41a is arranged at the exit end 41 of the light guide 40 that is opposite to the entrance end of the light guide 40 optically connected to the light source unit 20. The exit end face 41a includes a distal end face of the core 43a and a distal end face of the cladding 43b.

The light guide 40 is an elongated member that is bendable by an external force.

The exit end 41 of the light guide 40 including the exit end face 41a is inserted into a ferrule 45 in engagement therewith and is protected by the ferrule 45. The distal end of the ferrule 45 including the exit end 41 is inserted into a holding hole 61 (to be described later) of the holder 60 so that the exit end face 41a is optically connected to the first light conversion member 50. The distal end face of the ferrule 45 is a flat face and is arranged substantially in the same plane as the exit end face 41a.

The ferrule 45 is tubular and has, for example, a cylindrical shape. The ferrule 45 is made of, for example, a ceramic mainly composed of zirconia or a metal such as nickel.

The illumination unit 30 is optically connected to the light source unit 20 and receives the primary light emitted from the light source unit 20. The illumination unit 30 emits illumination light generated based on the primary light. Specifically, the illumination unit 30 converts the optical characteristics of at least part of the primary light to generate secondary light. The secondary light has optical characteristics different from the optical characteristics of the primary light. The optical characteristics include, for example, a wavelength. For example, the illumination unit 30 absorbs part of the primary light and converts the absorbed primary light into secondary light that is wavelength-converted light having a wavelength range different from the wavelength range of the primary light. The illumination unit 30 emits both the primary light and the secondary light as illumination light. The illumination light is only required to include light (e.g., the secondary light) that has optical characteristics different from the optical characteristics of the primary light. In other words, the illumination light only needs to include at least light (e.g., the secondary light) other than the primary light.

The illumination unit 30 emits illumination light to the opposite side to the light source unit 20 in order to illuminate the object with the illumination light. For example, the illumination unit 30 emits illumination light from the illumination unit 30 to the outside of the illumination unit 30. The outside of the illumination unit 30 indicates the forward region of an insertion section 220, which will be described later, and the outside region of the insertion section 220. Specifically, the illumination unit 30 emits illumination light from the holder exit portion 69 toward the forward region of the holder exit portion 69. For example, the forward region of the insertion section 220 and the forward region of the holder exit portion 69 indicate the right side in FIG. 2A, and is the opposite side to the arrangement positions of the light source unit 20 and light guide 40 in the central axis C direction. Therefore, the illumination light indicates light emitted from the illumination unit 30 to the outside of the illumination unit 30.

For example, the first light conversion member 50 includes a first wavelength conversion member configured to convert at least part of primary light into secondary light, first wavelength-converted light having a wavelength different from the wavelength of the primary light, and emits the secondary light.

The first wavelength conversion member has a first phosphor. For example, the first phosphor absorbs at least part of blue laser light that is primary light irradiating the first phosphor, wavelength-converts the absorbed blue laser light into yellow fluorescence that is first wavelength-converted light (secondary light), and emits this secondary light. The center wavelength of the fluorescence is, for example, 550 nm. The first phosphor emits fluorescence isotropically from the entire circumference of the first phosphor.

The first phosphor is represented by, for example, a composition of $Y_3Al_5O_{12}$:Ce (hereinafter referred to as YAG). In the present embodiment, the first phosphor is, for example, polycrystallized YAG ceramics. The YAG ceramics has an optical property of transmitting most of the primary light and secondary light therethrough without scattering them. The YAG ceramics have a high thermal conductivity of approximately 10 W/mK.

The first light conversion member 50 may have, for example, a YAG single crystal (not shown). The first light conversion member 50 may include a powdery YAG phosphor and a first containing member that contains the YAG phosphor. The composition of the YAG phosphor is substantially the same as the composition of the first phosphor. The YAG phosphor is dispersed inside the first containing member and sealed by the first containing member. The first containing member is, for example, glass or silicone resin.

The first light conversion member 50 has a desired value as efficiency for converting the amount of absorbed primary light into the amount of first wavelength-converted light (hereinafter referred to as internal quantum efficiency). Specifically, the first light conversion member 50 has an internal quantum efficiency of approximately 80%.

Therefore, when the first light conversion member 50 performs wavelength conversion, approximately 80% of the light amount of primary light absorbed by the first light conversion member 50 is wavelength-converted, and approximately 20% of the light amount is lost. The approximately 20% of the lost light is converted into heat. As described, when the first light conversion member 50 performs wavelength conversion, the first light conversion member 50 has a property of generating heat in an amount corresponding to the conversion loss simultaneously with the wavelength conversion.

The first light conversion member 50 has a columnar shape, for example, a cylindrical shape. The first light conversion member 50 may have a rectangular column shape. The first light conversion member 50 may be obtained by truncating a cone in a plane parallel to the bottom face of the cone. Examples of the first light conversion member 50 include a truncated cone shape.

The first light conversion member 50 includes a first face 51 configured to receive primary light, a second face 53 facing the first face 51, and a side face 55 surrounding the portion between the first face 51 and second face 53. The primary light irradiates most of the first face 51. The first face 51 and the second face 53 are, for example, substantially perpendicular to the central axis C, are flat faces, have substantially the same area, and have substantially the same diameter.

When the secondary light is isotropically emitted from the first light conversion member 50, for example, the secondary light is emitted rearward from the first face 51, forward from the second face 53 and sideways from the side face 55.

The holder 60 includes, for example, metal brass. The holder 60 may include a metal such as aluminum or copper, or a metal compound such as aluminum nitride.

The holder 60 has a holding hole 61 in which the ferrule 45 is arranged, and a hollow portion 63 in which the first light conversion member 50 is arranged. The holding hole 61 and the hollow portion 63 are arranged along the central axis C direction, and are continuous with each other in the central axis C direction inside the holder 60. The holding hole 61 and the hollow portion 63 constitute a through-hole that passes through the inside of the holder 60 in the central axis C direction. Thus, the holder 60 is tubular.

The holding hole 61 has a columnar shape, for example, a cylindrical shape. The diameter of the holding hole 61 is slightly larger than the diameter of the ferrule 45. The holding hole 61 is continuous with an introduction port 61a from which the ferrule 45 is introduced into the holding hole 61. The introduction port 61a is a hole for introducing the exit end 41 into the holder 60 through the holding hole 61. The ferrule 45 may be fitted in the holding hole 61. The holding hole 61 indirectly holds the exit end 41 by means of the ferrule 45 inserted into the holding hole 61. The ferrule 45 may be omitted, in which case the holding hole 61 is thin, the exit end 41 is directly inserted into the holding hole 61, and the holding hole 61 directly holds the exit end 41 inserted into the holding hole 61.

The hollow portion 63 has a rear hollow portion 63a and a front hollow portion 63b. The rear hollow portion 63a and the front hollow portion 63b are arranged along the central axis C direction and are continuous with each other in the central axis C direction inside the holder 60. The rear hollow portion 63a is arranged between the holding hole 61 and front hollow portion 63b, and is continuous with the holding hole 61 and the front hollow portion 63b. The front hollow portion 63b is arranged on the opposite side to the holding hole 61 with respect to the rear hollow portion 63a. The holder entrance portion 67 and a light transmission member 93, which will be described later, are arranged in the rear hollow portion 63a, and the first light conversion member 50, the light transmission member 93 and the holder exit portion 69, which will be described later, are arranged in the front hollow portion 63b.

Figure 2B:
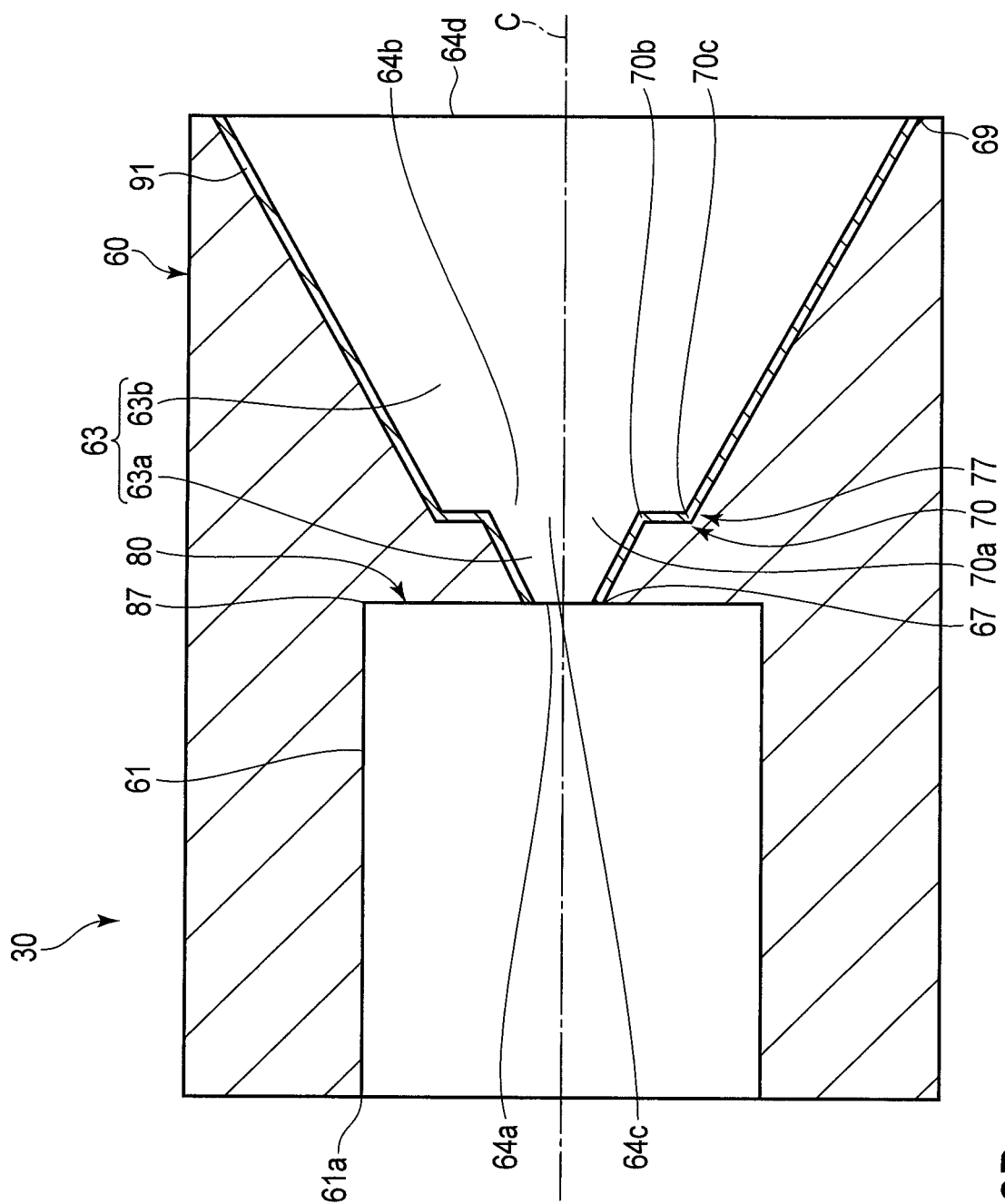
FIG. 2B is a cross-sectional view of a holder arranged in the illumination unit shown in FIG. 2A.

The rear hollow portion 63a and the front hollow portion 63b have, for example, a truncated cone shape. The shapes of the rear hollow portion 63a and front hollow portion 63b are not limited to particular ones. As shown in FIG. 2B, the rear hollow portion 63a and the front hollow portion 63b respectively have bottom faces 64a and 64b and top faces 64c and 64d that are arranged in a substantially perpendicular direction, substantially perpendicular to the central axis C direction. The top faces 64c and 64d are arranged on the front side (on the side of the holder exit portion 69), and the bottom faces 64a and 64b are arranged on the rear side (on the side of the holder entrance portion). In the continuous portion between the rear hollow portion 63a and the front hollow portion 63b, the bottom face 64b of the front hollow portion 63b of the truncated cone is continuous with the top face 64c of the rear hollow portion 63a of the truncated cone, is placed on the top face 64c of the rear hollow portion 63a, and is larger than the top face 64c of the rear hollow portion 63a. Therefore, in the continuous portion, a first fixing portion 70, which is a stepped portion, is arranged on the inner peripheral face of the holder 60. The diameter of the bottom face 64a of the rear hollow portion 63a is smaller than the diameter of the top face 64c of the rear hollow portion 63a, the diameter of the top face 64c of the rear hollow portion 63a is smaller than the diameter of the bottom face 64b of the front hollow portion 63b, the diameter of the bottom face 64b of the front hollow portion 63b is smaller than the diameter of the top face 64d of the front hollow portion 63b.

As can be seen from this, in the rear hollow portion 63a and the front hollow portion 63b, the inner diameter of the holder 60 gradually increases from the rear toward the front in the central axis C direction, and the inner peripheral face of the holder 60 in the hollow portion 63 is a tapered surface. Specifically, the inner diameter of the holder 60 in the rear hollow portion 63a gradually increases in the central axis C direction from the holder entrance portion 67, which will be described later, toward the first fixing portion 70, which is a stepped portion. Further, the inner diameter of the holder 60 in the hollow portion 63 (the front hollow portion 63b) gradually increases from the first fixing portion 70 toward the holder exit portion 69, described later, in the central axis C direction. Thus, the holder 60 has a tapered structure. The inner diameter of the holder 60 increases at the step portion between the rear hollow portion 63a and the front hollow portion 63b.

The holder 60 includes a holder entrance portion 67 that the primary light enters, and a holder exit portion 69 from which illumination light including at least secondary light is emitted. The holder entrance portion 67 and the holder exit portion 69 are names of portions of the holder 60. The holder entrance portion 67 is arranged rearward, the holder exit portion 69 is arranged forward, and the first light conversion member 50 is arranged between the holder entrance portion 67 and the holder exit portion 69. For example, the holder entrance portion 67 is arranged on the bottom face 64a of the rear hollow portion 63a, and the holder exit portion 69 is arranged on the top face 64d of the front hollow portion 63b. Thus, the hollow portion 63 communicates with the holder entrance portion 67 and the holder exit portion 69.

The holder entrance portion 67 and the holder exit portion 69 are holes. The holder entrance portion 67 faces the first face 51 of the first light conversion member 50. The diameter of the holder entrance portion 67 is substantially the same as the diameter of the exit end face 41a, is smaller than the diameter of the first face 51, and is smaller than the diameter of the holder exit portion 69. The diameter of the holder entrance portion 67 may be larger than the diameter of the exit end face 41a. The holder exit portion 69 faces the second face 53 of the first light conversion member 50. The holder exit portion 69 has a diameter larger than the diameter of the first light conversion member 50, that is, it is larger than the second face 53.

The holder 60 has a first fixing portion 70 arranged between the holder entrance portion 67 and the holder exit portion 69 in the central axis C direction. In the present embodiment, the first fixing portion 70 is arranged away from the holder exit portion 69 and is arranged close to the holder entrance portion 67. Specifically, the first fixing portion 70 is arranged closer to the holder entrance portion 67 than the holder exit portion 69, and is located closer to the holder entrance portion 67 than the middle position between the holder entrance portion 67 and the holder exit portion 69 in the central axis C direction. The first fixing portion 70 is arranged on a flat region substantially perpendicular to the central axis C of the primary light and on the inner peripheral face of the holder 60 in the hollow portion 63. The first fixing portion 70 functions as a step portion in the continuous portion between the rear hollow portion 63a and the front hollow portion 63b. For example, the first fixing portion 70 is arranged over the entire peripheral face and has a ring shape. The outer diameter and inner diameter of the first fixing portion 70 are larger than the diameter of the holder entrance portion 67 and smaller than the diameter of the holder exit portion 69. The first fixing portion 70 is a flat face, faces the holder exit portion 69, and is substantially parallel to the holder exit portion 69. The first fixing portion 70 may be arranged in at least part of the peripheral face.

Figure 2C:
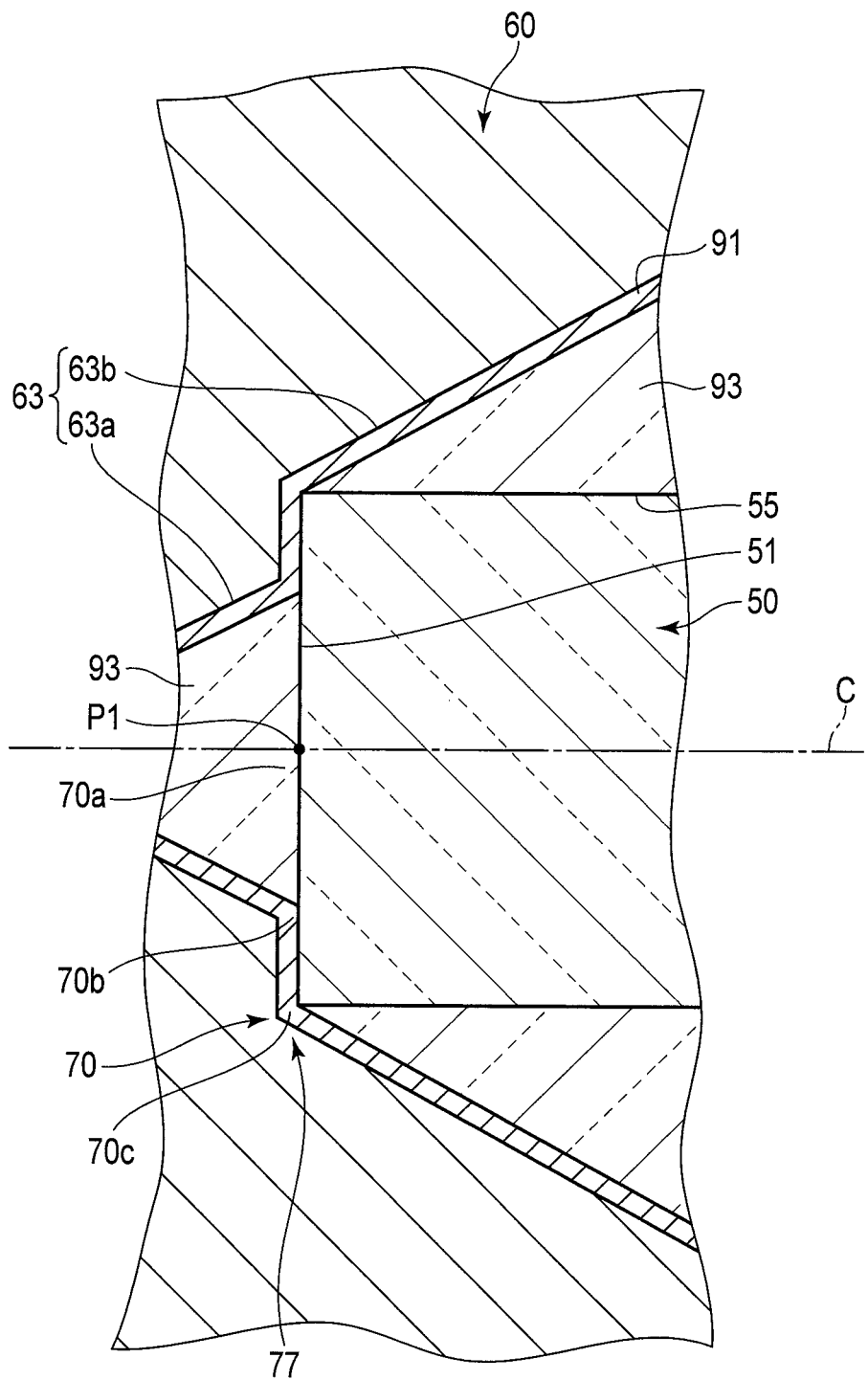
FIG. 2C is an enlarged view of the portion near a first fixing portion arranged in the illumination unit shown in FIG. 2A.

The ring-shaped first fixing portion 70 has a light transmission region 70a through which primary light traveling from the holder entrance portion 67 to the first light conversion member 50 is transmitted. As shown in FIGS. 2B and 2C, the light transmission region 70a is a region surrounded by the inner peripheral portion 70b of the ring-shaped first fixing portion 70, and the outer diameter of the light transmission region 70a corresponds to the inner diameter of the first fixing portion 70. The light transmission region 70a is larger than a beam spot that the primary light emitted from the exit end face 41a forms on the first face 51 of the first light conversion member 50, and is smaller than the first face 51. Specifically, the diameter of the light transmission region 70a is smaller than the diameter of the first face 51, is sufficiently larger than the diameter of the beam spot, and is sufficiently larger than the diameter of the holder entrance portion 67.

The first fixing portion 70 fixes the first light conversion member 50 in the central axis C direction so that the first light conversion member 50 is located between the holder entrance portion 67 and the holder exit portion 69. For example, the first fixing portion 70 fixes the first light conversion member 50 to the front hollow portion 63b of the hollow portion 63. At least a portion of the first fixing portion 70 that is a flat face is in contact with a portion of the first face 51 of the first light conversion member 50. Specifically, the first face 51 is arranged on the first fixing portion 70 so that the first face 51 is arranged away from the holder entrance portion 67 and the first face 51 covers the light transmission region 70a. With this arrangement, the peripheral end portion of the first face 51 comes into contact with the first fixing portion 70, and the first light conversion member 50 is fixed thereby. The peripheral end portion is a portion other than the region covering the light transmission region 70a, has a ring shape, and exposes part of the first face 51 described above. The "contact" mentioned here indicates, for example, surface contact, and the surface contact indicates that the entire portion of the first face 51 facing the first fixing portion 70 comes into contact with the entire first fixing portion 70. In other words, the first face 51 of the first light conversion member 50 is placed on the first fixing portion 70, and the first fixing portion 70 supports the first face 51. Thus, the first fixing portion 70 functions as a receiving portion configured to receive the first light conversion member 50. When the first light conversion member 50 is fixed, the first face 51 excluding the peripheral end portion thereof constitutes most of the first face 51, covers the entire light transmission region 70a, and receives the primary light transmitted through the light transmission region 70a.

The first face 51 and the first fixing portion 70, which are in contact with each other, may be bonded to each other with, for example, an adhesive. The adhesive is, for example, a transparent resin.

When the first light conversion member 50 is fixed, the side face 55 of the first light conversion member 50 is located away from the inner peripheral face of the holder 60 and from a reflection member 91 described later. When the first light conversion member 50 is fixed, the second face 53 of the first light conversion member 50 is located in the hollow portion 63 in a state where the second face 53 is away from the holder exit portion 69.

Since the first face 51 covers the light transmission region 70a and the first face 51 is in contact with the first fixing portion 70, the diameter of the first face 51 of the first light conversion member 50 is larger than the diameter of the light transmission region 70a and is substantially the same as the outer diameter of the first fixing portion 70. As long as the first face 51 can come into contact with the first fixing portion 70, the diameter of the first face 51 may be smaller than the outer diameter of the first fixing portion 70.

The first fixing portion 70 fixes the first light conversion member 50 so that the first face 51 of the first light conversion member 50 is arranged along a direction substantially perpendicular to the central axis C. The "substantially perpendicular" as used herein allows an inclination of approximately 0° to 5° with respect to the exact perpendicularity to the central axis C. Such an inclination is allowed because it does not affect the desired performance of the illumination device 10 of emitting illumination light with little variation in optical characteristics.

Wavelength-converted light (secondary light) is generated and is isotropically emitted from a region including a substantial light emitting point P1 (see FIG. 2C). The light emitting point P1 is an intersection between the first face 51 and the central axis C, and is a substantial light emitting point of the first light conversion member 50. Therefore, the first fixing portion 70 should fix the first light conversion member 50 so that the first face 51 on which the light emitting point P1 is arranged is arranged along the substantially perpendicular direction. Since the first fixing portion 70 is arranged between the holder entrance portion 67 and the holder exit portion 69, the first fixing portion 70 controls the arrangement position of the first light conversion member 50 including the point P1 between the holder entrance portion 67 and the holder exit portion 69 and within the holder 60. Because of the surface contact between the first face 51 and the first fixing portion 70, the first fixing portion 70 stably positions the first light conversion member 50 including the light emitting point P1, between the holder entrance portion 67 and the holder exit portion 69 and within the holder 60.

As shown in FIG. 2B and FIG. 2C, the inner peripheral portion 70b of the first fixing portion 70 is continuous with the peripheral end at the front of the rear hollow portion 63a. In the central axis C direction and from the holder entrance portion 67 to the inner peripheral portion 70b of the first fixing portion 70, that is, in the rear hollow portion 63a, the inner diameter of the holder 60 gradually increases, and the inner peripheral face of the holder 60 is tapered.

As shown in FIG. 2B and FIG. 2C, the outer peripheral portion 70c of the first fixing portion 70 is continuous with the peripheral end at the rear of the front hollow portion 63b. In the central axis C direction and from the outer peripheral portion 70c of the first fixing portion 70 to the holder exit portion 69, that is, in the front hollow portion 63b, the inner diameter of the holder 60 gradually increases, and the inner peripheral face of the holder 60 is tapered.

Although not shown, where the first light conversion member 50 has, for example, a truncated cone shape, the first face 51 that is the top face of the truncated cone may be in contact with the first fixing portion 70, and the side face 55 that is the peripheral face of the truncated cone may be in contact with the tapered surface.

For example, where the first light conversion member 50 has a spherical shape, part of the first light conversion member 50 is fixed to part of the first fixing portion 70. The "fixing" mentioned here indicates point contact, and the point contact is intended to refer to, for example, contact in a narrower range than surface contact. As can be seen from this, part of the first light conversion member 50 may be in contact with at least part of the first fixing portion 70.

As shown in FIGS. 2A, 2B, and 2C, the holder 60 has a first positioning portion 77 that is arranged between the holder entrance portion 67 and the holder exit portion 69 in the central axis C direction, and that is configured to position the first light conversion member 50 in the substantially perpendicular direction. The first positioning portion 77 is a boundary portion between the outer peripheral portion 70c of the first fixing portion 70 and the internal peripheral face of the holder 60 in the front hollow portion 63b, and is a continuous portion between the outer peripheral portion 70c and the peripheral edge at the rear of the front hollow portion 63b. In the present embodiment, the first positioning portion 77 is arranged over the entire inner peripheral face of the holder 60 in the front hollow portion 63b, and the diameter of the first face 51 is substantially the same as the outer diameter of the first fixing portion 70. Therefore, the outer peripheral portion of the first face 51 is in engagement with the entire periphery of the first positioning portion 77. By this engagement, the first positioning portion 77 positions the first light conversion member 50 so that the first face 51 does not separate from the first fixing portion 70 in the substantially perpendicular direction. The first positioning portion 77 is only required to position at least the first face 51. At least part of the outer peripheral portion of the first face 51 may be in contact with the first positioning portion 77.

The diameter of the first face 51 may be smaller than the outer diameter of the first fixing portion 70, and the outer peripheral portion of the first face 51 may be separate from the first positioning portion 77 and does not have to be in contact with the first positioning portion 77. In this case, the first fixing portion 70 and the first face 51 may be bonded to each other with, for example, an adhesive in a state where the first face 51 is positioned in the substantially perpendicular direction. In this manner, positioning is performed. The side face 55 reliably separates from the tapered surface, so that the extraction efficiency of secondary light is increased.

The holder 60 includes a second fixing portion 80 that is arranged in substantially the same plane as the holder entrance portion 67. The second fixing portion 80 is a bottom face of the holder 60 in the holding hole 61 and is a flat face that is arranged along the substantially perpendicular direction, which is substantially perpendicular to the central axis C direction. The second fixing portion 80 is arranged substantially parallel to the first fixing portion 70.

The second fixing portion 80 fixes the exit end 41 between the introduction port 61a and the holder entrance portion 67 in the central axis C direction. Specifically, the second fixing portion 80 fixes the exit end 41 by means of the ferrule 45. In more detail, when the ferrule 45 is inserted into the holding hole 61, the distal end face of the ferrule 45 including the exit end face 41a comes into contact with the second fixing portion 80 so that the exit end face 41a is optically connected to the first light conversion member 50. The "contact" mentioned here indicates surface contact, and the surface contact indicates that the entire portion of the ferrule 45 facing the second fixing portion 80 comes into contact with the entire second fixing portion 80. By this contact, the exit end 41 is fixed in the central axis C direction. At this time, the exit end face 41a of the exit end 41 and the holder entrance portion 67 are arranged in substantially the same plane and are optically connected to each other. Thus, the second fixing portion 80 functions as a receiving portion configured to receive the ferrule 45.

For example, the diameter of the second fixing portion 80 corresponds to the diameter of the holding hole 61, is larger than the diameter of the holder entrance portion 67, is larger than the inner diameter and outer diameter of the first fixing portion 70, and is smaller than the diameter of the holder exit portion 69.

The holder 60 is arranged on the inner peripheral face of the holder 60 in the holding hole 61 and is arranged between the introduction port 61a and the holder entrance portion 67. The holder includes a second positioning portion 87 configured to position the exit end 41 in the substantially perpendicular direction. The second positioning portion 87 functions as a boundary portion between the inner peripheral face of the holder 60 and the second fixing portion 80 (bottom face) in the holding hole 61. The second positioning portion 87 is arranged on the entire inner peripheral face of the holder 60 in the holding hole 61, and the diameter of the ferrule 45 is substantially the same as the diameter of the holding hole 61. Therefore, the outer peripheral portion 45c at the distal end of the ferrule 45 comes into engagement with the second positioning portion 87. By this engagement, the second positioning portion 87 positions the ferrule 45 so that the distal end portion of the ferrule 45 does not separate from the second fixing portion 80 in the direction substantially perpendicular to the central axis C direction. At least part of the outer peripheral portion 45c of the ferrule 45 may be in contact with the second positioning portion 87. The second positioning portion 87 may include the inner peripheral face of the holder 60 in the holding hole 61.

By the positioning of the ferrule 45, the exit end 41 is positioned. That is, the second positioning portion 87 indirectly acts on the exit end face 41a and the exit end 41 by means of the ferrule 45. Therefore, the outer peripheral portion of the exit end 41 is in indirect contact with the second positioning portion 87, with the ferrule 45 interposed. The exit end face 41a is positioned in the substantially perpendicular direction by the second positioning portion 87. As described above, the ferrule 45 may be omitted. In this case, the outer peripheral portion of the exit end 41 may be in direct contact with the second positioning portion 87.

Where the diameter of the holding hole 61 is larger than the diameter of the ferrule 45, the outer peripheral portion 45c at the distal end of the ferrule 45 may be away from the second positioning portion 87 and may not be in contact with the second positioning portion 87. In this case, the second fixing portion 80 and the ferrule 45 may be bonded to each other with, for example, an adhesive.

The illumination unit 30 includes a reflection member 91 configured to reflect the light irradiating the reflection member 91 toward the holder exit portion 69. The light irradiating the reflection member 91 includes, for example, primary light and secondary light. The reflection member 91 reflects the light traveling forward toward the holder exit portion 69. The reflection member 91 reflects the secondary light emitted from the first light conversion member 50 and irradiating the reflection member 91 toward the holder exit portion 69. That is, the reflection member 91 reflects the secondary light emitted from the second face 53 and side face 55 of the first light conversion member 50, so that the secondary light emitted from the second face 53 and side face 55 of the first light conversion member 50 travels to the holder exit portion 69 without entering the first light conversion member 50. Further, the reflection member 91 reflects return light that returns (travels) from the front (the side of the holder exit portion 69) to the rear (the side of the holder entrance portion 67) toward the holder exit portion 69. The return light indicates light traveling in the opposite direction of the illumination light in the central axis C direction, indicates light traveling from the front to the rear, and indicates light traveling toward the light source unit 20. For example, the reflection member 91 reflects toward the holder exit portion 69 the primary light and secondary light (wavelength-converted light) that are return light returning from the first face 51 of the first light conversion member 50 to the side of the holder entrance portion 67.

The reflection member 91 preferably has a high reflectance with respect to the primary light and the secondary light. When the primary light and the secondary light enter the reflection member 91, the reflection member 91 regularly reflects or diffusely reflects the primary light and the secondary light.

The reflection member 91 is arranged on the inner peripheral face of the holder 60 in the hollow portion 63. Specifically, the reflection member 91 is arranged on the inner peripheral face existing from the holder entrance portion 67 to the first fixing portion 70, on the first fixing portion 70, and on the inner peripheral face existing from the first fixing portion 70 to the holder exit portion 69. The reflection member 91 may be arranged on at least part of the inner peripheral face.

The reflection member 91 of the present embodiment is, for example, a metal reflection film (reflection mirror) formed by plating a thin metal, such as silver or aluminum, on the inner peripheral face. The reflection member 91 may be protected by a protection film (not shown). The protection film covers the reflection member 91. The protection film is a member having a high transmittance; for example, it is a metal oxide film such as silicon dioxide or conductive glass.

The illumination unit 30 includes a light transmission member 93 that is arranged in the hollow portion 63 and transmits primary light and secondary light therethrough. The light transmission member 93 is arranged between the holder entrance portion 67 and the first face 51, on the side of the side face 55, and between the second face 53 and the holder exit portion 69.

The light transmission member 93 is preferably made of glass such as quartz or a transparent silicone resin. The light transmission member 93 is preferably a transparent member. However, the light transmission member 93 is not necessarily limited to these. The light transmission member 93 has a truncated cone shape in the rear hollow portion 63a. The light transmission member 93 has a truncated cone shape with a recessed bottom face in the front hollow portion 63b. The entire peripheral face of the light transmission member 93 is in contact with the inner peripheral face of the holder 60, with the reflection member 91 interposed. The light transmission member 93 is in contact with the entire second face 53 and entire side face 55 of the first light conversion member 50 and with part of the first face 51 of the first light conversion member 50. The part of the first face 51 refers to a portion that is not arranged on the first fixing portion 70. The exit face of the light transmission member 93 is arranged in the holder exit portion 69 and has a diameter larger than those of the holder entrance portion 67 and the first and second faces 51 and 53 of the light conversion member. From the exit face, illumination light is emitted forward.

The exit end 41 including the exit end face 41a, the ferrule 45, the first light conversion member 50, the holder 60, the reflection member 91, and the light transmission member 93 are arranged as being rotation symmetric, with the central axis C as a center. The exit end 41 including the exit end face 41a, the ferrule 45, the first light conversion member 50, the reflection member 91, and the light transmission member 93 are arranged inside the holder 60.

Figure 3B:
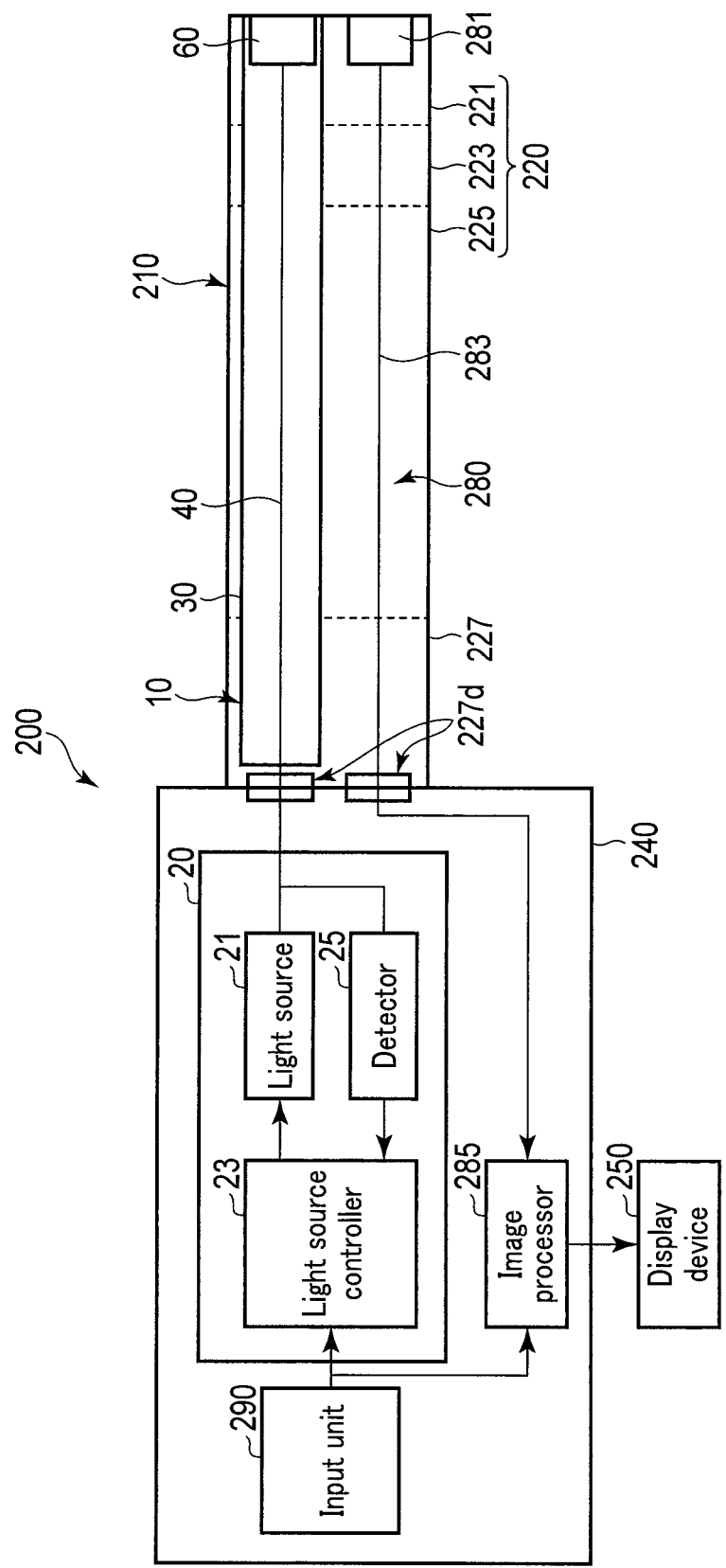
FIG. 3B is a diagram showing a configuration of the endoscope system shown in FIG. 3A.

An endoscope system 200 equipped with the illumination device 10 will be described with reference to FIG. 3A and FIG. 3B.

The endoscope system 200 includes, for example, an endoscope 210 configured to emit illumination light to a target object and to take an image of the target object, and a control device 240 that is removably connected to the endoscope 210. The target object is, for example, an affected portion or a disease portion of a body cavity. The endoscope system 200 includes a display device 250 that is connected to the control device 240 and has, for example, a monitor for displaying the target object imaged by the endoscope 210. The endoscope system 200 also includes an imaging unit 280 for imaging.

The endoscope 210 includes: a hollow elongated insertion section 220 to be inserted into, for example, a body cavity; and a control section 227 coupled to the proximal end of the insertion section 220 and enabling the endoscope 210 to be operated.

The insertion section 220 includes, from its distal end side to its proximal end side, a distal end hard section 221, a bendable section 223, and a flexible tube section 225. The proximal end of the distal end hard section 221 is coupled to the distal end of the bendable section 223, and the proximal end of the bendable section 223 is coupled to the distal end of the flexible tube section 225. The flexible tube section 225 extends from the control section 227.

The control section 227 includes: a bend control section 227a with which the bendable section 223 is bent; a switch section 227b that is operated to supply air and/or water, to perform suction or to perform imaging, and a universal cord 227c connected to the control section 227.

The universal cord 227c extends from a side portion of the control section 227. The connector 227d of the universal cord 227c is detachable from the control device 240.

The control device 240 controls the driving of the illumination device 10, the endoscope 210, the display device 250, and the imaging unit 280.

The imaging unit 280 includes: an imager 281 configured to capture an image of a target object; an imaging cable 283 configured to transmit the image captured by the imager 281 as an electrical signal, and an image processor 285 configured to process an image transmitted by the imaging cable 283. The images processed by the image processor 285 are displayed on the display device 250. The imager 281 is arranged in the distal end hard section 221, the image processor 285 is arranged in the control device 240, and the imaging cable 283 is arranged inside the endoscope 210. The imager 281 has, for example, a CCD or a CMOS. The image processor 285 processes an image based on an instruction input from an input unit 290 electrically connected to the image processor 285.

The light source unit 20 is provided for the control device 240. The illumination unit 30 is incorporated in the endoscope 210. Specifically, the exit end 41 of the light guide 40 and the holder 60 are arranged inside the distal end hard section 221 and are adjacent to the imager 281.

The light source unit 20 includes a light source 21, a light source controller 23 configured to control the light source 21, a beam splitter (not shown), a pinhole (not shown), and a detector 25.

The light source controller 23 controls the light source 21 based on an instruction input from the input unit 290 electrically connected to the light source controller 23. The light source controller 23 controls, for example, the light quantity of the light source 21. Thereby, illumination light having a desired brightness is generated.

The beam splitter is arranged between the light source 21 and the entrance end of the light guide 40. The beam splitter transmits primary light traveling from the light source 21 to the entrance end therethrough, and reflects secondary light that is return light returning from the entrance end to the light source 21. The pinhole has a hole through which at least part of the secondary light reflected by the beam splitter passes. The detector 25 detects the secondary light that has passed through the hole. The detector 25 includes, for example, a photodiode. The secondary light, which is the return light, is reflected by the beam splitter, travels through the hole, and travels to the detector 25. The detector 25 outputs light quantity information regarding the light quantity of the return light (secondary light) to the light source controller 23. The light source controller 23 controls the light quantity of the light source 21 based on the light quantity information.

The input unit 290 inputs an instruction to start an operation of the endoscope system 200 including the illumination device 10. The input unit 290 has, for example, a switch. The input unit 290 is provided for, for example, the control device 240.

The light source controller 23 and the image processor 285 are consisted by a hardware circuit including, for example, an ASIC. At least one of the light source controller 23 and the image processor 285 may be constituted by a processor. Where at least one of these is constituted by a processor, an internal memory or an external memory (neither is shown) accessible by the processor is arranged. The internal memory or the external memory stores program code for causing the processor to function as at least one of them when executed by the processor.

Figure 4B:
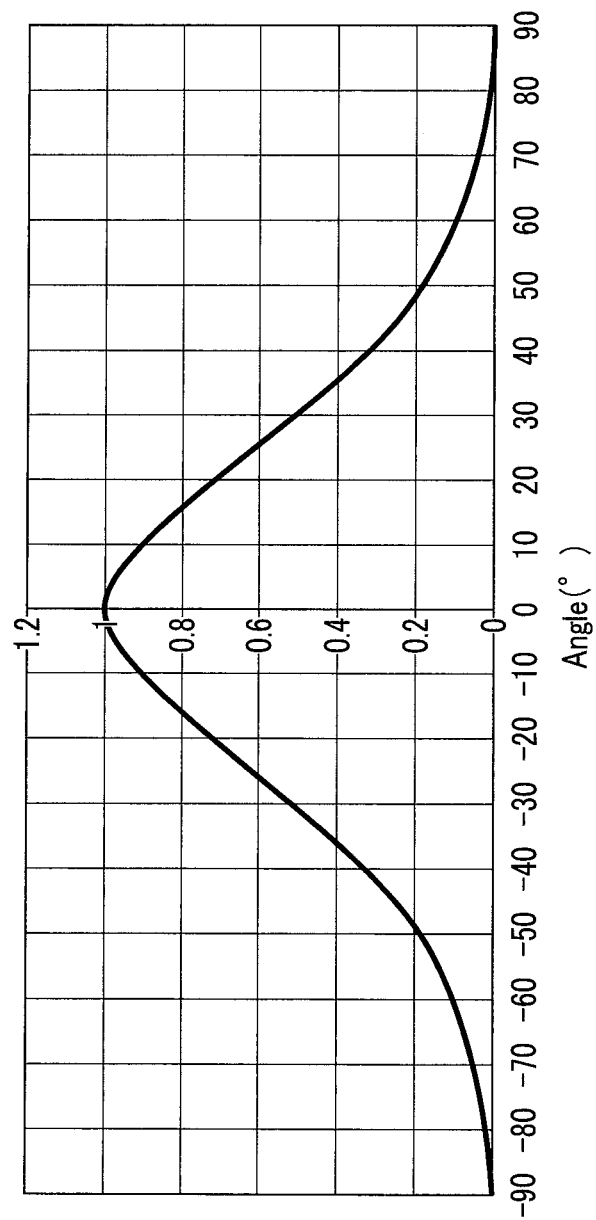
FIG. 4B is a diagram showing light distribution characteristics that the secondary light has in the illumination unit shown in FIG. 4A.

Next, a description will be given, with reference to FIG. 4A and FIG. 4B, of an example of an operation in which illumination light is generated by the illumination unit 30 and emitted from the illumination unit 30 to the forward region of the illumination unit 30.

The primary light, which is blue laser light, is emitted from the light source 21 and guided by the light guide 40. The primary light is emitted from the exit end face 41a toward the first light conversion member 50. The light distribution of the primary light emitted from the exit end face 41a is narrow, and the light distribution half-value angle of the primary light is, for example, approximately 15°. The intensity of the primary light is highest on the central axis C.

The primary light enters the light transmission member 93 arranged in the rear hollow portion 63a from the holder entrance portion 67 and travels inside the light transmission member 93. The primary light is emitted from the light transmission member 93, passes through the light transmission region 70a, and irradiates the first face 51 of the first light conversion member 50. A beam spot of the primary light is formed on the first face 51. The diameter of the beam spot is set in accordance with the distance between the exit end face 41a and the first face 51 in the central axis C direction, the light distribution characteristics of the primary light emitted from the exit end face 41a, the refractive index of the light transmission member 93, etc. In the present embodiment, the diameter of the beam spot is set so that it is smaller than the diameters of the light transmission region 70a and first face 51.

The first light conversion member 50 made of YAG ceramics has an optical property of permitting most of the primary light, not wavelength-converted by the YAG ceramics and passing through the YAG ceramics, to be transmitted through without diffusion. Therefore, part of the primary light irradiating the first light conversion member 50 is not wavelength-converted or diffused by the first light conversion member 50, passes through the first light conversion member 50, and is emitted forward from the first light conversion member 50. Most of the primary light emitted forward from the first light conversion member 50 travels through the inside of the light transmission member 93 arranged in the front hollow portion 63b, and does not travel toward the reflection member 91 but travels directly to the holder exit portion 69. The primary light is emitted directly from the holder exit portion 69 as illumination light. That is, the primary light is emitted as illumination light without the traveling direction of the primary light being changed by the reflection member 91. Although the description was given of the primary light emitted forward from the first light conversion member 50, this description is similarly applied to the primary light emitted sideways from the first light conversion member 50.

The remaining part of the primary light irradiating the first light conversion member 50 is absorbed by the first light conversion member 50 and is converted by the first light conversion member 50 into secondary light that is first wavelength-converted light. The quantity of secondary light, the light conversion quantity, is proportional to the quantity of primary light that enters the first light conversion member 50.

The secondary light is isotropically emitted from the first light conversion member 50. Specifically, the secondary light is emitted from the first light conversion member 50 forward, sideways, and rearward. The light distribution angle of the secondary light is different from the light distribution angle of the primary light.

Although not shown, part of the secondary light emitted forward from the second face 53 of the first light conversion member 50 travels through the inside of the light transmission member 93 arranged in the front hollow portion 63b, and travels to the reflection member 91, irradiating the reflection member 91. The secondary light is reflected forward by the reflection member 91, thereby changing the traveling direction of the secondary light. This secondary light is emitted from the holder exit portion 69 as illumination light without re-entering the first light conversion member 50. Although not shown, the remaining part of the secondary light emitted forward from the second face 53 of the first light conversion member 50 travels through the inside of the light transmission member 93 arranged in the front hollow portion 63b, and does not travel toward the reflection member 91 but travels directly to the holder exit portion 69. The secondary light is directly emitted from the holder exit portion 69 as illumination light. That is, the secondary light is emitted as illumination light without the traveling direction of the secondary light being changed by the reflection member 91.

The side face 55 of the first light conversion member 50 is away from the reflection member 91 arranged on the tapered surface. Further, the inner diameter of the holder 60 in the front hollow portion 63b is gradually decreased from the front to the rear. Therefore, part of the secondary light emitted from the side face 55 is reflected forward by the reflection member 91 and does not re-enter the first light conversion member 50. This secondary light is emitted from the holder exit portion 69 as illumination light without re-entering the first light conversion member 50. Although not shown, the remaining part of the secondary light emitted from the side face 55 travels through the inside of the light transmission member 93 arranged in the front hollow portion 63b, and does not travel toward the reflection member 91 but travels directly to the holder exit portion 69. The secondary light is directly emitted from the holder exit portion 69 as illumination light. That is, the secondary light is emitted as illumination light without the traveling direction of the secondary light being changed by the reflection member 91.

The inner diameter of the holder 60 in the rear hollow portion 63a is gradually decreased from the front toward the rear, and the reflection member 91 is arranged on the tapered surface of the rear hollow portion 63a. Therefore, although not shown, part of the secondary light emitted rearward from the first face 51 of the first light conversion member 50, which is return light, is reflected a number of times by the reflection member 91 and travels forward. This secondary light re-enters the first light conversion member 50 and passes through the first light conversion member 50 without the light distribution being converted by the first light conversion member 50 having the optical property of transmitting most of the secondary light therethrough. The secondary light is emitted from the first light conversion member 50 forward and sideways, and as mentioned above, is emitted from the holder exit portion 69 as illumination light.

Although not shown, the remaining part of the secondary light, which is return light, travels from the peripheral end portion of the first face 51 facing the first fixing portion 70 to the first fixing portion 70. The secondary light is also reflected forward by the reflection member 91 arranged on the first fixing portion 70. This secondary light re-enters the first light conversion member 50 and passes through the first light conversion member 50 without the light distribution being converted by the first light conversion member 50 having the optical property of transmitting most of the secondary light therethrough. The secondary light is emitted from the first light conversion member 50 forward and sideways, and as mentioned above, is emitted from the holder exit portion 69 as illumination light.

The first fixing portion 70 is arranged closer to the holder entrance portion 67 than the holder exit portion 69. Therefore, the first face 51 of the first light conversion member 50 including the light emitting point P1 is arranged inside the holder 60 and located closer to the holder entrance portion

67 than the holder exit portion 69. The component of the secondary light increases, which travels forward from the light emitting point P1 and whose light distribution is converted by the reflection member 91 arranged forward of the light emitting point P1. As a result, the secondary light that does not have isotropic light distribution but has narrow light distribution is emitted from the holder exit portion 69 as illumination light. Specifically, as shown in FIG. 4B, the light distribution half-value angle of the secondary light emitted from the holder exit portion 69 as illumination light is less than approximately 90°. The first fixing portion 70 is arranged closer to the holder entrance portion 67 than the middle position between the holder entrance portion 67 and the holder exit portion 69 in the central axis C direction. The first face 51 arranges the light emitting point P1 so that it is inside the holder 60 and closer to the holder entrance portion 67 than the middle position. Thereby, the light distribution half-value angle of the secondary light as illumination light is approximately 65° or less.

Where the light distribution half-value angle of the secondary light is approximately 65° or less, the distance between the holder entrance portion 67 and the first fixing portion 70 in the central axis C direction is, for example, 0.1 mm, and the distance between the holder entrance portion 67 and the holder exit portion 69 in the central axis C direction is, for example, 0.6 mm.

Where the first fixing portion 70 is close to the holder entrance portion 67, the first face 51 and the light emitting point P1 are close to the holder entrance portion 67. As a result, the intensity of the primary light at the light emitting point P1 increases, so that the first light conversion member 50 may be locally scorched or generate high heat, and the temperature loss of the first light conversion member 50 is likely to occur. If the primary light is converted into secondary light, the light conversion quantity varies depending on the light quantity and temperature of the primary light. In the present embodiment, therefore, the first fixing portion 70 is arranged at a desired distance from the holder entrance portion 67, thereby suppressing the variation of the light conversion quantity.

When the first light conversion member 50 converts primary light into secondary light, the first light conversion member 50 generates heat in accordance with the conversion loss. The quantity of heat is proportional to the quantity of primary light that enters the first light conversion member 50.

In the first light conversion member 50, most heat is generated at the light emitting point P1.

Since the first face 51 on which the light emitting point P1 is arranged is in contact with the first fixing portion 70, the heat generated from the light emitting point P1 is transferred to the first fixing portion 70 through the first face 51. The heat is then transferred from the first fixing portion 70 to the holder 60 and released from the holder 60 to the outside. The temperature rise at the light emitting point P1 is suppressed, and the variation of the light conversion quantity of the first light conversion member 50 caused by heat is suppressed.

In the present embodiment, the first fixing portion 70 is arranged between the holder entrance portion 67 and the holder exit portion 69, so that the first light conversion member 50 can be stably fixed by the first fixing portion 70 at a position that is a desired distance away from the holder entrance portion 67 and the holder exit portion 69. Therefore, the light emitting point P1 can be stably arranged inside the holder 60, and illumination light with little variation in optical characteristics can be emitted.

The first light conversion member 50 has a cylindrical shape, and the first face 51 of the first light conversion member 50 is in surface contact with the first fixing portion 70. Therefore, the light emitting point P1 can be reliably and stably arranged on the central axis C, the first face 51 including the light emitting point P1 can be arranged along a direction substantially perpendicular to the central axis C direction, and the first light conversion member 50 including the light emitting point P1 can be stably arranged. Hence, illumination light with little variation in optical characteristics can be emitted.

The light emitting point P1 is arranged away from the reflection member 91 arranged on the tapered surface. Therefore, when the light distribution of the secondary light is converted by the reflection member 91, illumination light with little variation in optical characteristics can be emitted.

The side face 55 of the first light conversion member 50 is away from the reflection member 91 arranged on the tapered surface. Therefore, part of the secondary light whose light distribution is converted by the reflection member 91 is emitted as illumination light without re-entering the first light conversion member 50. Thereby, high extraction efficiency with respect to illumination light can be realized. Since the reflection member 91 is arranged on the first fixing portion 70 as well, secondary light as return light can be reflected toward the holder exit portion 69, and high extraction efficiency with respect to illumination light can be realized.

The first fixing portion 70 is arranged closer to the holder entrance portion 67 than the holder exit portion 69. Thereby, illumination light with narrow light distribution can be emitted, and illumination light with high intensity can be emitted.

The first positioning portion 77 comes into contact with the outer peripheral portion of the first face 51 and thereby positions the first light conversion member 50. Thus, the first light conversion member 50 can be positioned in the substantially perpendicular direction, the arrangement position of the light emitting point P1 can be stabilized, and the arrangement position of the first light conversion member 50 can be stabilized.

When the ferrule 45 including the exit end face 41a is arranged in the holding hole 61, the distal end face of the ferrule 45 comes into contact with the second fixing portion 80 and is fixed to the second fixing portion 80. Therefore, the exit end face 41a can be easily positioned in the central axis C direction.

The second positioning portion 87 comes into contact with the outer peripheral portion 45c of the distal end portion of the ferrule 45 and positions the exit end face 41a and the exit end 41. Thereby, the exit end face 41a and the exit end 41 can be positioned in the substantially perpendicular direction, and the arrangement positions of the exit end face 41a and exit end 41 can be stabilized. The emission position of the primary light can also be stabilized.

The first and second positioning portions 77 and 87 stabilize the arrangement position of the light emitting point P1 and the emission position of the primary light, and the relative positions between these positions are controlled and stabilized in the substantially perpendicular direction. Therefore, in the first light conversion member 50, the variation in the irradiation position of the primary light can be reduced, and the variation in the secondary light that is return light returning from the first light conversion member 50 to the light guide 40 can be reduced.

Since the holder 60 arranged inside the thin insertion section 220 is small, the first fixing portion 70 cannot be easily worked as a flat face when the first fixing portion 70 is formed by cutting the holder 60. The same problem holds true for the case where the first fixing portion 70 is a separate member from the holder 60 and the first fixing portion 70 is a type attached to the holder 60. In the present embodiment, if only the first face 51 on which the light emitting point P1 is arranged can be arranged in the direction substantially perpendicular to the central axis C direction, the illumination device 10 can emit illumination light with little variation in optical characteristics. Since this desired performance of the illumination device 10 is ensured, the first fixing portion 70 is allowed to have a rough face, as shown in FIG. 5, and such a first fixing portion 70 is permissible. Similarly, even if burrs are present on the inner peripheral portion 70b and outer peripheral portion 70c of the first fixing portion 70, such a first fixing portion 70 is permissible.

The endoscope 210 may be connected to the control device 240 wirelessly. In this case, the light source unit 20 is incorporated in the control section 227. Therefore, the illumination device 10 is not limited to the one provided for both the endoscope 210 and the control device 240; it may be provided solely for the endoscope 210. As described above, at least part of the illumination device 10 may be provided for the endoscope 210.

[Modification 1]

Modification 1 of the present embodiment will be described with reference to FIG. 6. A description will be given only of the differences from the first embodiment.

The size of the light transmission region 70a is substantially the same as the size of the holder entrance portion 67. Specifically, the diameter of the light transmission region 70a is substantially the same as the diameter of the holder entrance portion 67. The diameter of the light transmission region 70a is larger than the diameter of the beam spot the primary light forms on the first face 51. Therefore, the rear hollow portion 63a has a columnar shape, for example, a cylindrical shape. In the rear hollow portion 63a, the inner diameter of the holder 60 is uniform from the holder entrance portion 67 to the first fixing portion 70 in the central axis C direction. Since the reflection member 91 is very thin, the diameter of the light transmission region 70a can be regarded as substantially the same as the diameter of the holder entrance portion 67 even though the reflection member 91 is arranged on the inner peripheral face of the holder 60 in the rear hollow portion 63a. The inner diameter of the first fixing portion 70 of this modification is smaller than the inner diameter of the first fixing portion 70 of the first embodiment. The diameter of the light transmission region 70a of this modification is smaller than the diameter of the light transmission region 70a of the first embodiment and is slightly larger than the diameter of the beam spot of the primary light. The diameter of the holder entrance portion 67 of this modification is slightly larger than the diameter of the holder entrance portion 67 of the first embodiment.

In the present modification, the area of the first fixing portion 70 can be increased compared to the first embodiment, and the contact area between the first fixing portion 70 and the first face 51 of the first light conversion member 50 can be increased. Therefore, the light emitting point P1 can be reliably arranged on the central axis C, and the first light conversion member 50 including the light emitting point P1 can be stably arranged. Further, the quantity of heat transferred from the first light conversion member 50 to the first fixing portion 70 increases due to the increase in the contact area. Therefore, the quantity of heat released from the holder 60 can be increased, and variations in the light conversion quantity of the first light conversion member 50 due to heat can be reliably suppressed.

[Modification 2]

Figure 7A:
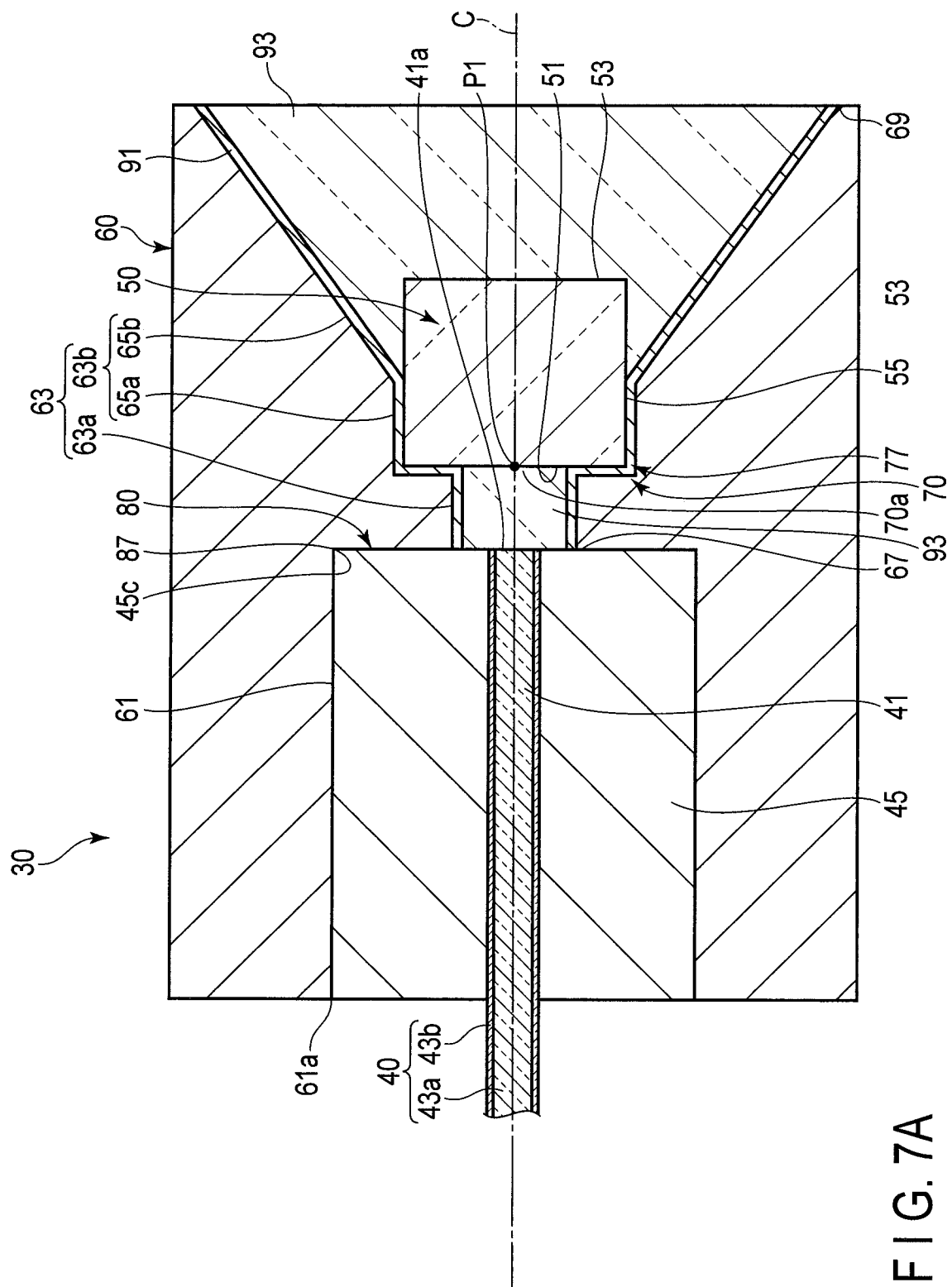
FIG. 7A is a diagram schematically showing an illumination unit according to modification 2 of the first embodiment.

Modification 2 of the embodiment will be described with reference to FIG. 7A. A description will be given only of the differences from modification 1.

The front hollow portion 63b has, for example, a shape that is a combination of a columnar shape and a truncated cone shape. The columnar shape is, for example, a cylindrical shape. The front end portion of the cylindrical portion 65a of the front hollow portion 63b is continuous with the rear end portion of the truncated cone portion 65b. The diameter of the cylindrical portion 65a is substantially the same as the diameter of the first light conversion member 50. The length of the cylindrical portion 65a is less than the length of the first light conversion member 50, and the rear end portion of the side face 55 of the first light conversion member 50 is in engagement with the inner peripheral face of the holder 60 in the cylindrical portion 65a.

In this modification, the light emitting point P1 can be reliably and stably arranged on the central axis C by the side face 55 of the first light conversion member 50 engaged with the inner peripheral face of the holder 60 in the cylindrical portion 65a. The first face 51 including the light emitting point P1 can be arranged along the direction substantially perpendicular to the central axis C direction, and the first light conversion member 50 including the light emitting point P1 can be reliably and stably arranged. Further, the side face 55 of the first light conversion member 50 can be stably arranged along the central axis C direction by the inner peripheral face of the holder 60 in the cylindrical portion 65a.

In this modification, heat can be transferred from the side face 55 to the holder 60. Therefore, the quantity of heat released from the holder 60 can be increased, and variations in the light conversion quantity of the first light conversion member 50 due to heat can be reliably suppressed. The present modification is also applicable to the first embodiment and modification 1.

Figure 7B:
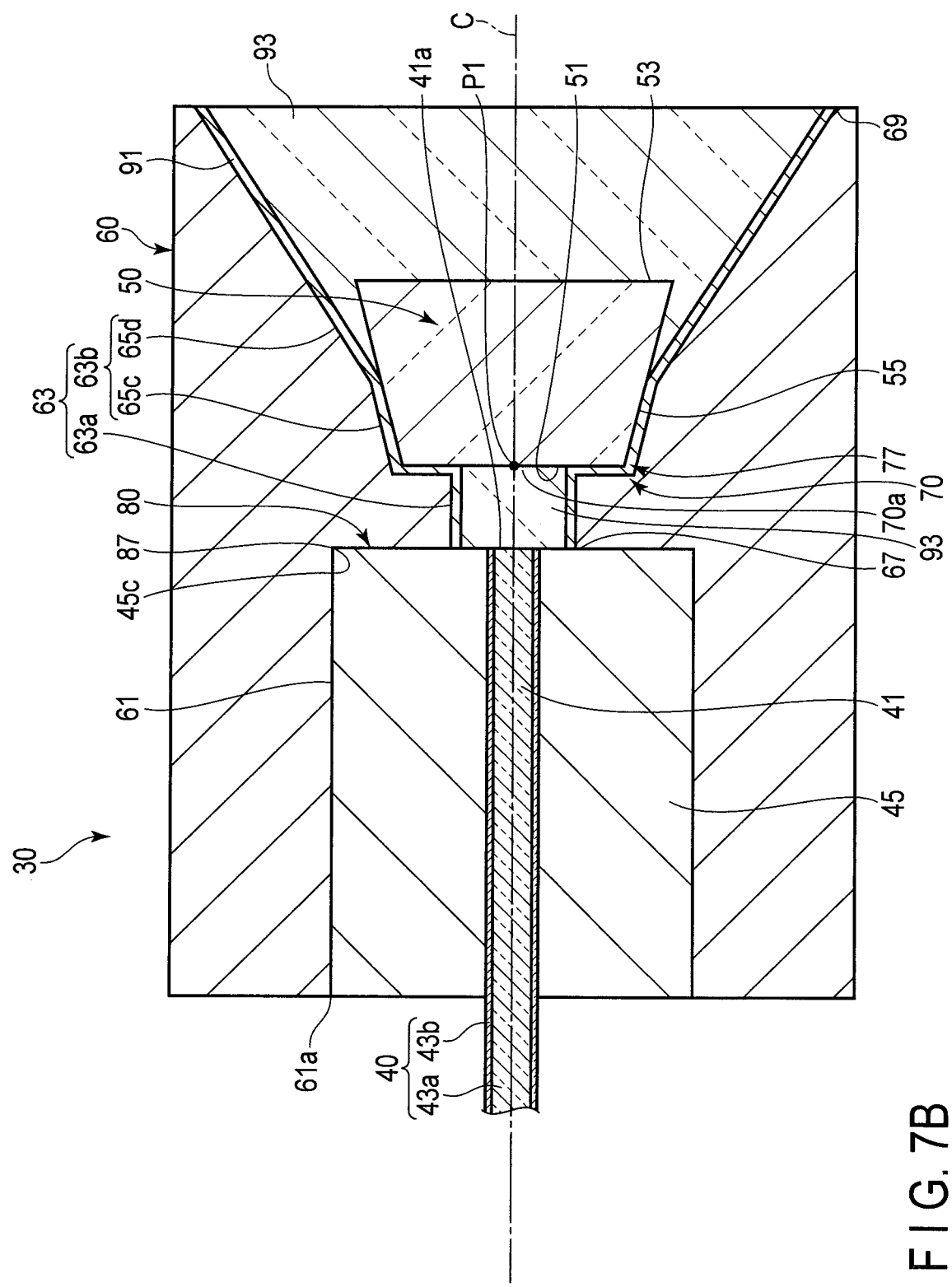
FIG. 7B is a diagram schematically showing the illumination unit according to modification 2 of the first embodiment.

As shown in FIG. 7B, the first light conversion member 50 that can be used may have a truncated cone shape. In this case, the front hollow portion 63b may have a shape that is a combination of a first truncated cone shape and a second truncated cone shape having a wider taper angle than the first truncated cone shape. For example, the front end portion of the first truncated cone portion 65c is continuous with the rear end portion of the second truncated cone portion 65d. The taper angle of the first truncated cone portion 65c is substantially the same as the taper angle of the first light conversion member 50. The length of the first truncated cone portion 65c is less than the length of the first light conversion member 50, and the rear end portion of the side face 55 of the first light conversion member 50 is in engagement with the inner peripheral face of the holder 60 in the first truncated cone portion 65c. Owing to this, the advantages of modification 2 are attained. The constitution shown in FIG. 7B is also applicable to the first embodiment and modification 1.

[Modification 3]

Modification 3 of the present embodiment will be described with reference to FIG. 8. A description will be given only of the differences from modification 1.

For example, the first light conversion member 50 includes a first diffusing member. The first diffusing member converts at least part of the primary light irradiating the first diffusing member into secondary light that has the same wavelength as the primary light without changing the wavelength of the primary light and has a light distribution angle different from the light distribution angle of the primary light. The first diffusing member converts the primary light into first diffused light with reduced coherence by widening the light distribution angle of the primary light and diffusing the primary light. The first diffusing member emits the secondary light. As can be seen from the above, the first diffusing member is a light distribution angle conversion member configured to emit secondary light having a light distribution angle different from the light distribution angle of the primary light irradiating the first diffusing member.

For example, the first diffusing member has first diffusion particles (not shown) and a second inclusion member (not shown) that includes the first diffusion particles.

The first diffusion particles are dispersed inside the second inclusion member and sealed by the second inclusion member. The first diffusion particles are fine particles of, for example, a metal, or a metal compound. Such first diffusion particles are particles of, for example, alumina, titanium oxide, and barium sulfate. The particle size of the first diffusion particles is several hundred nm to several tens of μm. The refractive index of the first diffusion particles is different from the refractive index of the second inclusion member. For example, the refractive index of the first diffusion particles is preferably higher than the refractive index of the second inclusion member. Owing to this, the first diffusion particles can provide improved light diffusion property.

The second inclusion member is formed of a member configured to transmit the primary light and secondary light therethrough. Such a second inclusion member is, for example, a transparent silicone resin or a transparent epoxy resin. The second inclusion member has a high transmittance with respect to the primary light and the secondary light. The second inclusion member seals included members. The second inclusion member may be glass that seals the first diffusion particles made of alumina.

The first diffusing member may have glass with a surface on which unevenness is arranged.

The light distribution characteristics of the secondary light that is the first diffused light emitted from the first diffusing member is desirably set based on the position of the light emitting point P1, the reflection at the reflection member 91 arranged on the tapered surface, and the light distribution conversion quantity attributable to the concentration of the first diffusion particles in the second inclusion member and the thickness of the first diffusing member.

A description will be given of an example of an operation in which illumination light is emitted from the illumination unit 30 to the forward region of the illumination unit 30.

As in the first embodiment, primary light irradiates the first face 51 of the first light conversion member 50.

Although not shown, part of the primary light irradiating the first face 51 of the first light conversion member 50 is not diffused by the first light conversion member 50, passes through the first light conversion member 50, and is emitted forward from the first light conversion member 50. Although not shown, most of the primary light emitted forward from the first light conversion member 50 travels through the inside of the light transmission member 93 arranged in the front hollow portion 63b, and does not travel toward the reflection member 91 but travels directly to the holder exit portion 69. The primary light is emitted directly from the holder exit portion 69 as illumination light. That is, the primary light is emitted as illumination light without the traveling direction of the primary light being changed by the reflection member 91.

The remaining part of the primary light irradiating the first face 51 of the first light conversion member 50 is converted by the first light conversion member 50 into secondary light that is first diffused light. The wavelength of the first diffused light is the same as the wavelength of the primary light.

Part of the secondary light that is the first diffused light is emitted forward from the second face 53 of the first light conversion member 50, travels through the inside of the light transmission member 93 arranged in the front hollow portion 63b, and does not travel toward the reflection member 91 but travels directly to the holder exit portion 69. The secondary light is directly emitted from the holder exit portion 69 as illumination light. That is, the secondary light is emitted as illumination light without the traveling direction of the secondary light being changed by the reflection member 91. Although not shown, the remaining part of the secondary light that is the first diffused light is emitted forward from the second face 53 of the first light conversion member 50, travels through the inside of the light transmission member 93 arranged in the front hollow portion 63b, and travels to the reflection member 91, irradiating the reflection member 91. The secondary light is reflected forward by the reflection member 91, thereby changing the traveling direction of the secondary light. This secondary light is emitted from the holder exit portion 69 as illumination light without re-entering the first light conversion member 50.

The side face 55 of the first light conversion member 50 is away from the reflection member 91 arranged on the tapered surface. Also, the inner diameter of the holder 60 in the front hollow portion 63b is gradually decreased from the front to the rear. Therefore, although not shown, part of the secondary light, which is first diffused light, and emitted from the side face 55 is reflected forward by the reflection member 91 so that it does not re-enter the first light conversion member 50. This secondary light is emitted from the holder exit portion 69 as illumination light without re-entering the first light conversion member 50. Although not shown, the remaining part of the secondary light that is the first diffused light and emitted from the side face 55 travels through the inside of the light transmission member 93 arranged in the front hollow portion 63b, and does not travel toward the reflection member 91 but travels directly to the holder exit portion 69. The secondary light is directly emitted from the holder exit portion 69 as illumination light. That is, the secondary light is emitted as illumination light without the traveling direction of the secondary light being changed by the reflection member 91.

Although not shown, part of the secondary light (the first diffused light) that is return light travels from the peripheral end portion of the first face 51 facing the first fixing portion 70 to the first fixing portion 70. This secondary light is reflected forward by the reflection member 91 arranged on the first fixing portion 70. This secondary light re-enters the first light conversion member 50 and passes through the first light conversion member 50 without the light distribution being converted by the first light conversion member 50 having the optical property of transmitting most of the secondary light therethrough. The secondary light is emitted from the first light conversion member 50 forward and sideways, and as mentioned above, is emitted from the holder exit portion 69 as illumination light.

In the present modification, even where the first diffused light is used, the light emitting point P1 can be reliably and stably arranged on the central axis C, the first face 51 including the light emitting point P1 can be arranged along the direction substantially perpendicular to the central axis C direction, and the first light conversion member 50 including the light emitting point P1 can be stably arranged. Hence, illumination light with little variation in optical characteristics can be emitted. The present modification is also applicable to the first embodiment and modifications 1 and 2.

[Modification 4]

Figure 9B:
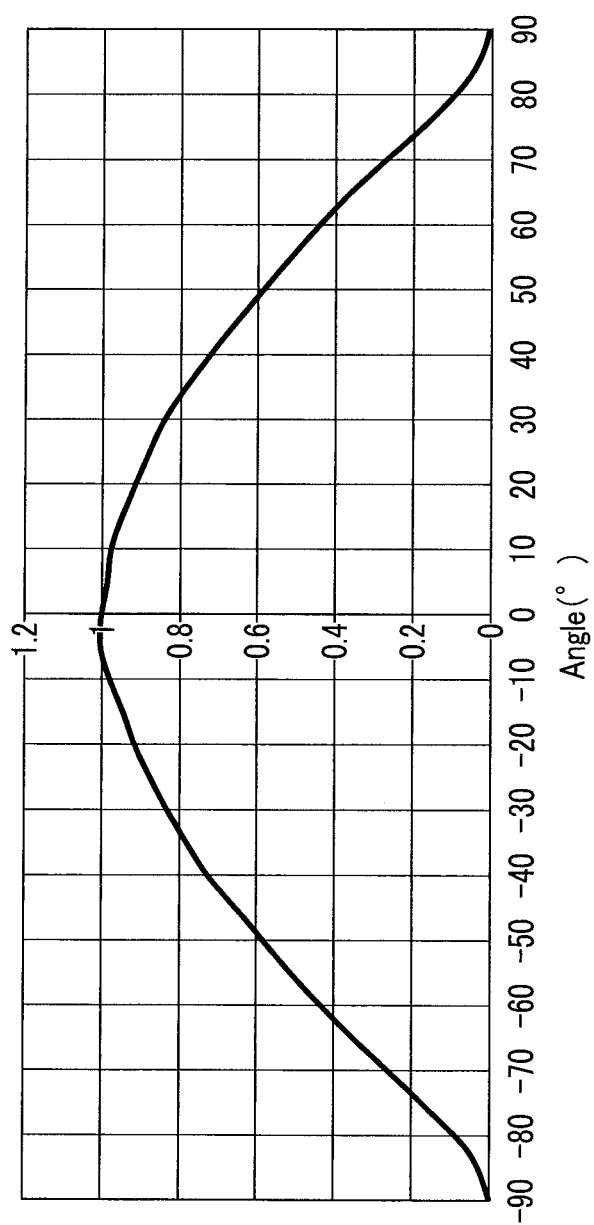
FIG. 9B is a diagram showing light distribution characteristics that the secondary light has in the illumination unit shown in FIG. 9A.

Modification 4 of the present embodiment will be described with reference to FIGS. 9A and 9B. A description will be given only the differences from the first embodiment.

The first fixing portion 70 is arranged away from the holder entrance portion 67 and is arranged close to the holder exit portion 69. Specifically, the first fixing portion 70 is arranged closer to the holder exit portion 69 than the holder entrance portion 67, and is located closer to the holder exit portion 69 than the middle position between the holder entrance portion 67 and the holder exit portion 69 in the central axis C direction. Therefore, the light emitting point P1 is arranged closer to the holder exit portion 69 than the holder entrance portion 67. As shown in FIG. 9A, the second face 53 may be arranged in substantially the same plane as the holder exit portion 69.

With respect to the secondary light (first wavelength-converted light) that is emitted from the first light conversion member 50, which is the first phosphor, in a wide range without directivity, the ratio of the secondary light traveling forward without traveling to the reflection member 91 increases from the corresponding ratio of the first embodiment. Therefore, secondary light having wide light distribution is emitted as illumination light. As shown in FIG. 9B, the light distribution half-value angle of the secondary light emitted from the holder exit portion 69 is, for example, 90° or more.

In this modification, in the illumination unit 30 configured to emit illumination light with wide light distribution, the primary light can be stably converted into secondary light.

Since the first face 51 and the light emitting point P1 are away from the holder entrance portion 67, the beam spot which the primary light forms on the first face 51 can be widened, and the intensity of the primary light at the light emitting point P1 can be reduced. Therefore, the first light conversion member 50 is prevented from being locally scorched or generating high heat, and the temperature loss of the first light conversion member 50 can be decreased. The present modification is also applicable to the first embodiment and modifications 1 to 3.

Second Embodiment

Figure 10A:
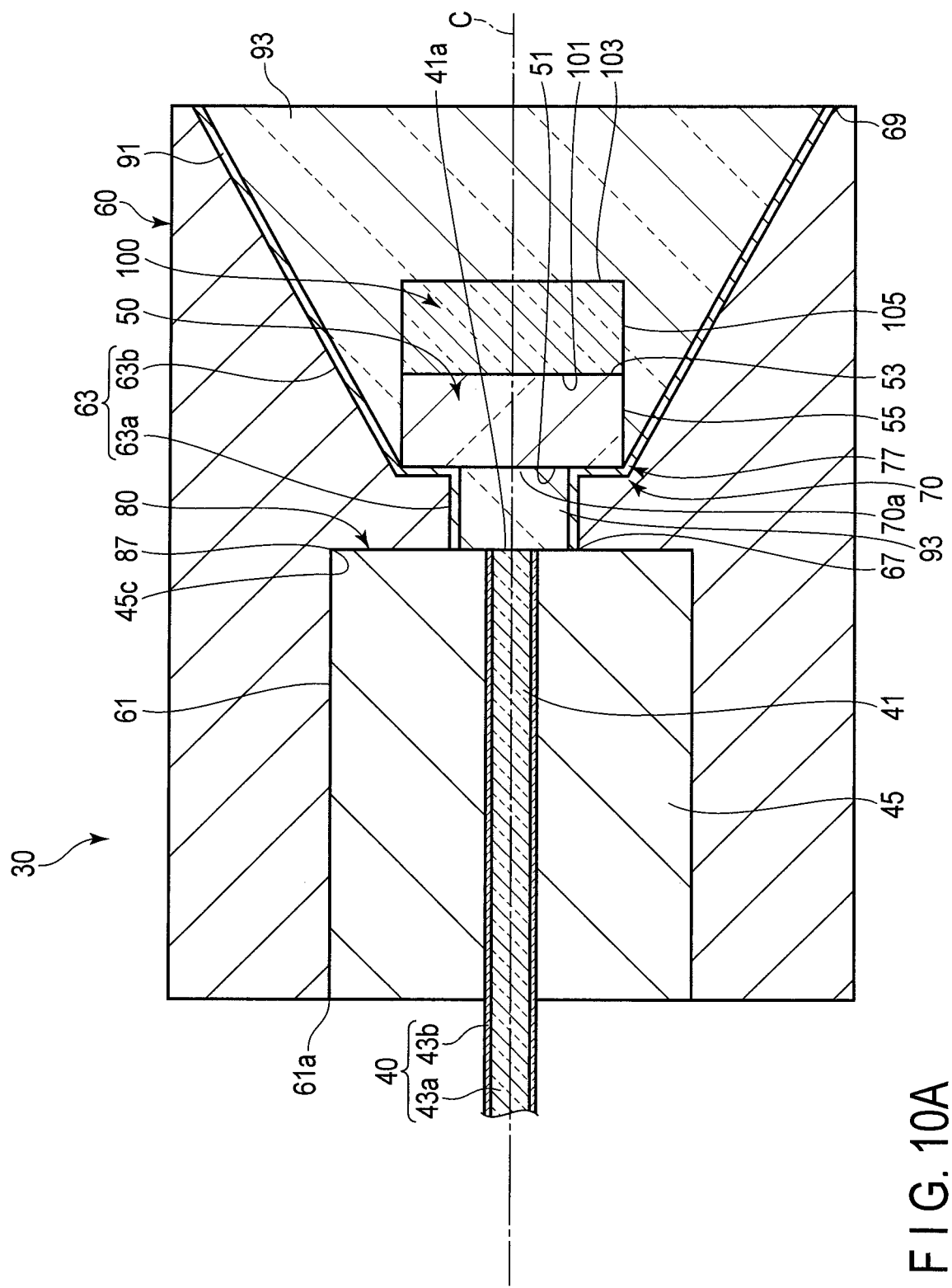
FIG. 10A is a diagram schematically showing an illumination unit according to the second embodiment.

The second embodiment of the present invention will be described with reference to FIGS. 10A and 10B. In the present embodiment, a description will be given only of the differences from the first embodiment.

The holder 60 includes a second light conversion member 100 configured to convert at least part of primary light into tertiary light having optical characteristics different from the optical characteristics of the primary light and secondary light. For example, the second light conversion member 100 includes a second wavelength conversion member configured to convert light into tertiary light, which is second wavelength-converted light having a wavelength different from the wavelengths of the primary and secondary light, and configured to emit the tertiary light.

The second wavelength conversion member has a second phosphor. For example, the second phosphor absorbs at least part of blue laser light that is primary light, wavelength-converts the absorbed blue laser light into green fluorescence that is second wavelength-converted light (tertiary light), and emits this tertiary light. The center wavelength of the green fluorescence is, for example, 532 nm. The second phosphor emits fluorescence isotropically from the entire periphery of the second phosphor.

The second phosphor is represented by, for example, a composition of $Lu_3Al_5O_{12}$:Ce (hereinafter referred to as LuAG). In the present embodiment, the second phosphor is, for example, polycrystallized LuAG ceramics. The second phosphor may be represented by a β-sialon composition. Such a second phosphor is sealed in silicone resin or glass.

The second light conversion member 100 has a columnar shape, for example, a cylindrical shape. The second light conversion member 100 may have a rectangular column shape. The second light conversion member 100 may have a shape obtained by truncating a cone in a plane parallel to the bottom face of the cone. Examples of such a second light conversion member 100 include a truncated cone shape.

The second light conversion member 100 includes a first face 101 configured to receive primary light, a second face 103 facing the first face 101, and a side face 105 surrounding the portion between the first face 101 and second face 103. The first face 101 and the second face 103 are, for example, substantially perpendicular to the central axis C, are flat faces, have substantially the same area and have substantially the same diameter.

When the tertiary light is isotropically emitted from the second light conversion member 100, for example, the tertiary light is emitted rearward from the first face 101, forward from the second face 103 and sideways from the side face 105.

The first face 101 has substantially the same area as the second face 53, and the diameter of the first face 101 is substantially the same as the diameter of the second face 53. The entire first face 101 is in contact with the entire second face 53, and the second light conversion member 100 is stacked on the first light conversion member 50. The "contact" mentioned here indicates surface contact, and the surface contact indicates, for example, that the entire portion of the first face 101 facing the second face 53 is in contact with the entire second face 53. At this time, the side face 55 of the second light conversion member 100 is arranged away from the inner peripheral face of the holder 60 and the reflection member 91. Further, the second face 103 of the second light conversion member 100 is located in the hollow portion 63 in a state where the second face 103 is away from the holder exit portion 69. The second face 53 and the first face 101 that are in contact with each other may be bonded to each other with, for example, an adhesive. The adhesive is, for example, a transparent resin. The diameter of the second light conversion member 100 may be larger than the diameter of the first light conversion member 50. Further, in order to stabilize the position of the second light conversion member 100, the second light conversion member 100 may be stacked on the first light conversion member 50 so that at least part of the outer periphery of the second light conversion member 100 is in contact with at least part of the tapered surface of the holder 60.

Since the first light conversion member 50 is stably arranged inside the holder 60 by the first fixing portion 70, the second light conversion member 100 can be stably arranged inside the holder 60 by stacking. The second face 53 functions as a third fixing portion that fixes the second light conversion member 100 stacked on the second face 53.

The second face 53 fixes the second light conversion member 100 so that the first face 101 of the second light conversion member 100 is arranged along a direction substantially perpendicular to the central axis C. The "substantially perpendicular" direction as used herein allows an inclination of about 0° to 5° with respect to the exact perpendicularity. Such an inclination is allowed because it does not affect the desired performance of the illumination device 10 of emitting illumination light with little variation in optical characteristics.

Second wavelength-converted light (tertiary light) is generated and isotropically emitted from a region including substantial light emitting point P2. The light emitting point P2 is an intersection between the first face 101 and the central axis C, and is a substantial light emitting point of the second light conversion member 100. Therefore, the second face 53 is only required to fix the second light conversion member 100 so that the first face 101 on which the light emitting point P2 is arranged is arranged along the substantially perpendicular direction. Also, the second face 53 is only required fix the second light conversion member 100 so that at least part of the first face 101 is arranged on the central axis C. Since the second face 53 is arranged between the holder entrance portion 67 and the holder exit portion 69, the second face 53 controls the arrangement position of the second light conversion member 100 including the light emitting point P2 between the holder entrance portion 67 and the holder exit portion 69 and within the holder 60. Because of the surface contact between the second face 53 and the first face 101, the second face 53 stably positions the first light conversion member 50 including the light emitting point P2 between the holder entrance portion 67 and the holder exit portion 69 and within the holder 60.

The second face 53 of the first light conversion member 50 and the first face 101 of the second light conversion member 100 are arranged closer to the holder entrance portion 67 than the holder exit portion 69. Specifically, the second face 53 and the first face 101 are arranged closer to the holder entrance portion 67 than the middle position between the holder entrance portion 67 and the holder exit portion 69 in the central axis C direction. Therefore, the light emitting point P2 is arranged closer to the holder exit portion 69 than the holder entrance portion 67.

The diameter of the first face 101 may be larger than the diameter of the second face 53. Therefore, the second light conversion member 100 may be arranged so as to cover the second face 53. As long as the second face 53 functions as the third fixing portion, at least part of the first face 101 may be in contact with at least part of the second face 53. The second light conversion member 100 may have a dome shape. The curved face of the dome is arranged on the second face 103.

A description will be given of an example of an operation in which illumination light is emitted from the illumination unit 30 to the forward region of the illumination unit 30.

Part of the primary light is emitted forward from the second face 53 of the first light conversion member 50 without being wavelength-converted and diffused by the first light conversion member 50. The primary light emitted forward from the second face 53 of the first light conversion member 50 irradiates the first face 101 of the second light conversion member 100. Part of the primary light is converted into tertiary light by the second light conversion member 100. The tertiary light is isotropically emitted from the second light conversion member 100. Specifically, the tertiary light is emitted from the second light conversion member 100 forward, sideways, and rearward. The light distribution angle of the tertiary light is different from the light distribution angle of the primary light.

Part of the tertiary light emitted forward from the second light conversion member 100 travels through the inside of the light transmission member 93 arranged in the front hollow portion 63b, and does not travel toward the reflection member 91 but travels directly to the holder exit portion 69. The tertiary light is emitted directly from the holder exit portion 69 as illumination light. That is, the tertiary light is emitted as illumination light without the traveling direction of the tertiary light being changed by the reflection member 91. Although not shown, the remaining part of the tertiary light emitted forward from the second light conversion member 100 travels through the inside of the light transmission member 93 arranged in the front hollow portion 63b, and travels to the reflection member 91, irradiating the reflection member 91. The tertiary light is reflected forward by the reflection member 91, thereby changing the traveling direction of the tertiary light. This tertiary light is emitted from the holder exit portion 69 as illumination light without re-entering the first light conversion member 50 and the second light conversion member 100.

The side face 55 of the second light conversion member 100 is arranged away from the reflection member 91 arranged on the tapered surface. Further, the inner diameter of the holder 60 in the front hollow portion 63b is gradually decreased from the front to the rear. Therefore, although not shown, part of the tertiary light emitted from the side face 55 is reflected forward by the reflection member 91 and does not re-enter the first light conversion member 50 or the second light conversion member 100. This tertiary light is emitted from the holder exit portion 69 as illumination light without re-entering the first light conversion member 50 and the second light conversion member 100. Although not shown, the remaining part of the tertiary light emitted from the side face 55 travels through the inside of the light transmission member 93 arranged in the front hollow portion 63b, and does not travel toward the reflection member 91 but travels directly to the holder exit portion 69. This tertiary light is emitted directly from the holder exit portion 69 as illumination light. That is, the secondary light is emitted as illumination light without the traveling direction of the secondary light being changed by the reflection member 91.

The first and second light conversion members 50 and 100 have an optical property of transmitting most of the secondary light and tertiary light therethrough. Although not shown, part of the tertiary light as the return light is transmitted through the first and second light conversion members 50 and 100 and travels from the peripheral portion of the first face 51 facing the first fixing portion 70 to the first fixing portion 70. The tertiary light is reflected forward by the reflection member 91 arranged on the first fixing portion 70. This tertiary light re-enters the first and second light conversion members 50 and 100 and passes through the first and second light conversion members 50 and 100 without the light distributions being converted by the first and second light conversion members 50 and 100. The tertiary light is emitted from the first light conversion members 50 and 100 forward and sideways, and as mentioned above, are emitted from the holder exit portion 69 as illumination light.

The second face 53 that is a third fixing portion is arranged closer to the holder entrance portion 67 than the middle position. Therefore, the first face 101 of the second light conversion member 100 including the light emitting point P2 is arranged inside the holder 60 and located closer to the holder entrance portion 67 than the middle position between the holder entrance portion 67 and the holder exit portion 69. With this constitution, the light distribution half-value angle of the tertiary light emitted from the holder exit portion 69 as illumination light is less than approximately 90°.

On the central axis C, the light emitting point P2 is arranged away from the light emitting point P1 by the thickness of the first light conversion member 50. The light emitting points P1 and P2 are arranged closer to the holder entrance portion 67 than the middle position between the holder entrance portion 67 and the holder exit portion 69 in the central axis C direction. As a result, the half-value distribution angles of the secondary light and tertiary light are less than approximately 90°, and the secondary light and the tertiary light are emitted as illumination light in the state where the light distributions of the secondary light and tertiary light are the same.

In the present embodiment, the second light conversion member 100 is stably fixed by the first face 51 of the first light conversion member 50 stably arranged inside the holder 60 by the first fixing portion 70 and the second face 53 facing the first face 51. Therefore, the light emitting point P2 can be stably arranged inside the holder 60, and illumination light with little variation in optical characteristics can be emitted.

The second light conversion member 100 has a cylindrical shape, and the first face 101 of the second light conversion member 100 is in surface contact with the second face 53. Therefore, the light emitting point P2 can be reliably and stably arranged on the central axis C, the first face 101 including the light emitting point P2 can be arranged along a direction substantially perpendicular to the central axis C direction, and the second light conversion member 100 including the light emitting point P2 can be stably arranged. Hence, illumination light with little variation in optical characteristics can be emitted.

The light emitting point P2 is arranged away from the reflection member 91 arranged on the tapered surface. Therefore, when the light distribution of the secondary light is converted by the reflection member 91, illumination light with little variation in optical characteristics can be emitted.

The side face 105 of the second light conversion member 100 is arranged away from the reflection member 91 arranged on the tapered surface. Therefore, part of the tertiary light whose light distribution is converted by the reflection member 91 is emitted as illumination light without re-entering the second light conversion member 100. Therefore, high extraction efficiency with respect to illumination light can be realized.

The third fixing portion is arranged closer to the holder entrance portion 67 than the holder exit portion 69, and the light emitting point P2 as well as the light emitting point P1 is arranged closer to the holder entrance portion 67 than the middle position. Thereby, illumination light with narrow light distribution can be emitted, light distribution characteristics with less color unevenness can be realized, and illumination light with high center intensity can be emitted.

[Modification 1]

Figure 11:
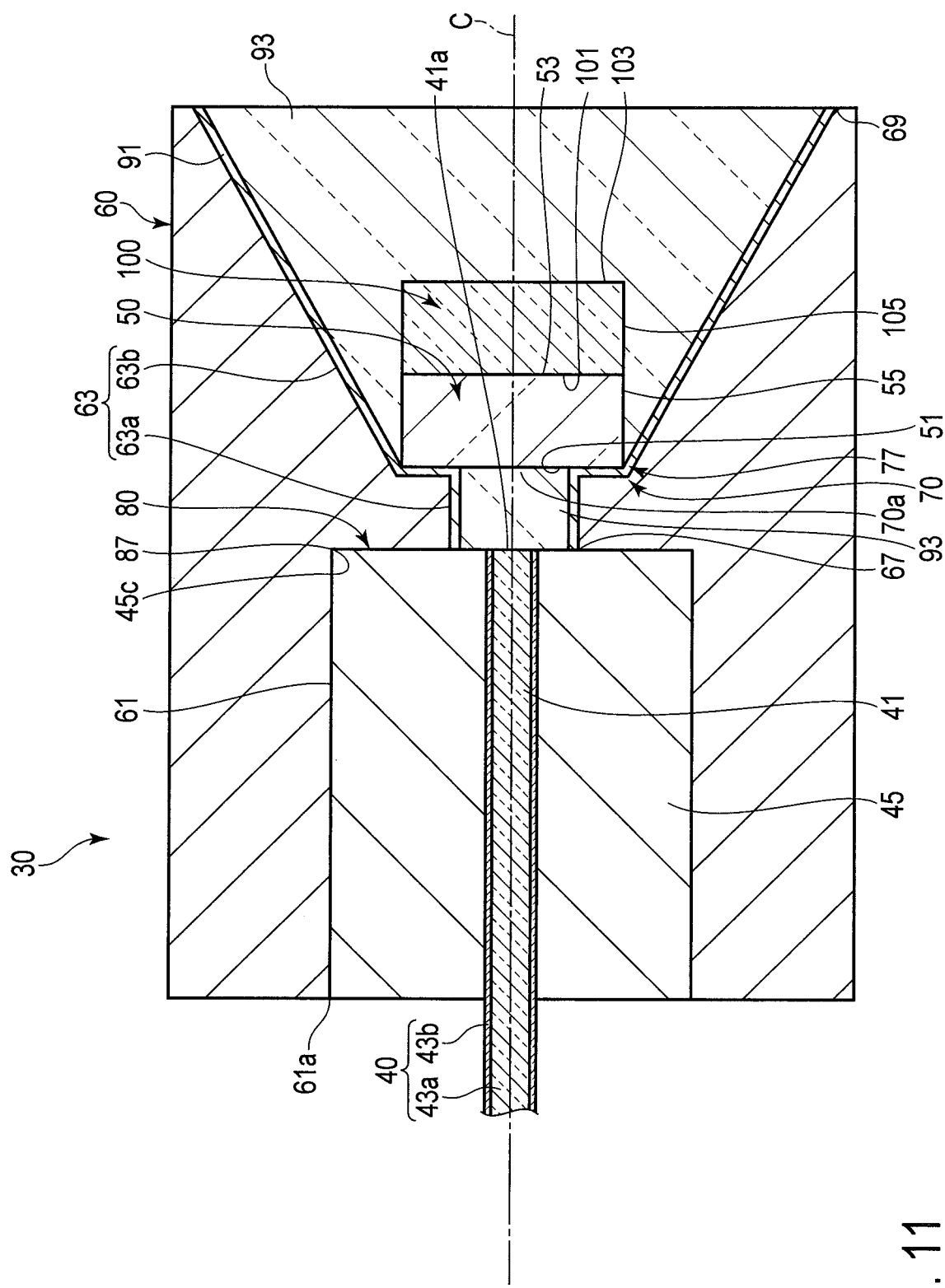
FIG. 11 is a diagram schematically showing an illumination unit according to modification 1 of the second embodiment.

Modification 1 of the present embodiment will be described with reference to FIG. 11. A description will be given only of the differences from the second embodiment.

The second light conversion member 100 includes a second diffusing member (not shown) in addition to the second phosphor. The second diffusing member converts at least part of the primary light irradiating the second diffusing member into tertiary light that is second diffused light that has the same wavelength as the primary light without changing the wavelength of the primary light and that has light distribution different from the light distribution of the primary light. The second diffusing member converts the primary light into second diffused light with reduced coherence by widening the light distribution angle of the primary light and diffusing the primary light. The second diffusing member emits the second diffused light as tertiary light. As can be seen from this, the second diffusing member is a light distribution angle conversion member configured to emit tertiary light having a light distribution angle different from the light distribution angle of the primary light irradiating the second diffusing member.

For example, the second diffusing member has second diffusion particles (not shown) and a third inclusion member (not shown) that includes the second diffusion particles.

The second diffusion particles are dispersed inside the third inclusion member and sealed by the third inclusion member. The second diffusion particles are fine particles of, for example, a metal, or a metal compound. Such second diffusion particles are particles of, for example, alumina, titanium oxide, and barium sulfate. The particle size of the second diffusion particles is several hundred nm to several tens of μm. The refractive index of the second diffusion particles is different from the refractive index of the third inclusion member. For example, the refractive index of the second diffusion particles is preferably higher than the refractive index of the third inclusion member. Owing to this, the second diffusion particles can provide improved light diffusion property.

The third inclusion member is formed of a member configured to transmit the primary light, secondary light, and tertiary light therethrough. Such a third inclusion member is, for example, a transparent silicone resin or a transparent epoxy resin. The third inclusion member has a high transmittance with respect to the primary light, secondary light, and tertiary light. The third inclusion member seals included members. The third inclusion member may be glass that seals the second diffusion particles made of alumina.

The second diffusing member may have glass with a surface on which unevenness is arranged.

With respect to the primary light that enters the second light conversion member 100, part of the primary light is converted into tertiary light (green fluorescence) by the second phosphor, and the remaining part of the primary light is converted into tertiary light (blue second diffused light) by the second diffusing member.

Although not shown, part of the tertiary light emitted forward from the second light conversion member 100 (green fluorescence (second wavelength-converted light) and blue second diffused light) travels through the inside of the light transmission member 93 arranged in the front hollow portion 63b, and does not travel toward the reflection member 91 but travels directly to the holder exit portion 69. The tertiary light (green fluorescence and blue second diffused light) is emitted from the holder exit portion 69 as illumination light. Although not shown, part of the tertiary light (green fluorescence and blue second diffused light) emitted forward from the second light conversion member 100 travels through the inside of the light transmission member 93 arranged in the front hollow portion 63b, and travels to the reflection member 91, irradiating the reflection member 91. The tertiary light is reflected forward by the reflection member 91, thereby changing the traveling direction of the tertiary light. This tertiary light is emitted from the holder exit portion 69 as illumination light without re-entering the first and second light conversion members 50 and 100. Although the description was given of the tertiary light emitted forward from the second light conversion member 100, this description is similarly applied to the tertiary light emitted sideways from the second light conversion member 100. Part of the primary light may pass through the second light conversion member 100. The primary light and the secondary light (first wavelength-converted light) are emitted as illumination light from the holder exit portion 69, as in the first embodiment.

The concentration of the second diffusion particles in the third inclusion member is adjusted as desired so that the light distribution characteristics of the tertiary light (second diffused light) emitted from the holder exit portion 69 are substantially the same as the light distribution characteristics of the secondary light and tertiary light (green fluorescence).

In this modification, the position of the light emitting point P2 on the central axis C can be adjusted by the second diffusing member, and the primary light can be stably converted into tertiary light (second diffused light).

Since the concentration of the second diffusion particles in the third inclusion member is adjusted as desired, illumination light can be emitted including tertiary light (second diffused light) whose light distribution characteristics are substantially the same as the light distribution characteristics of the secondary light (yellow fluorescence) and tertiary light (green fluorescence). The present modification is also applicable to the first embodiment and each of the aforementioned modifications.

Third Embodiment

Figure 12:
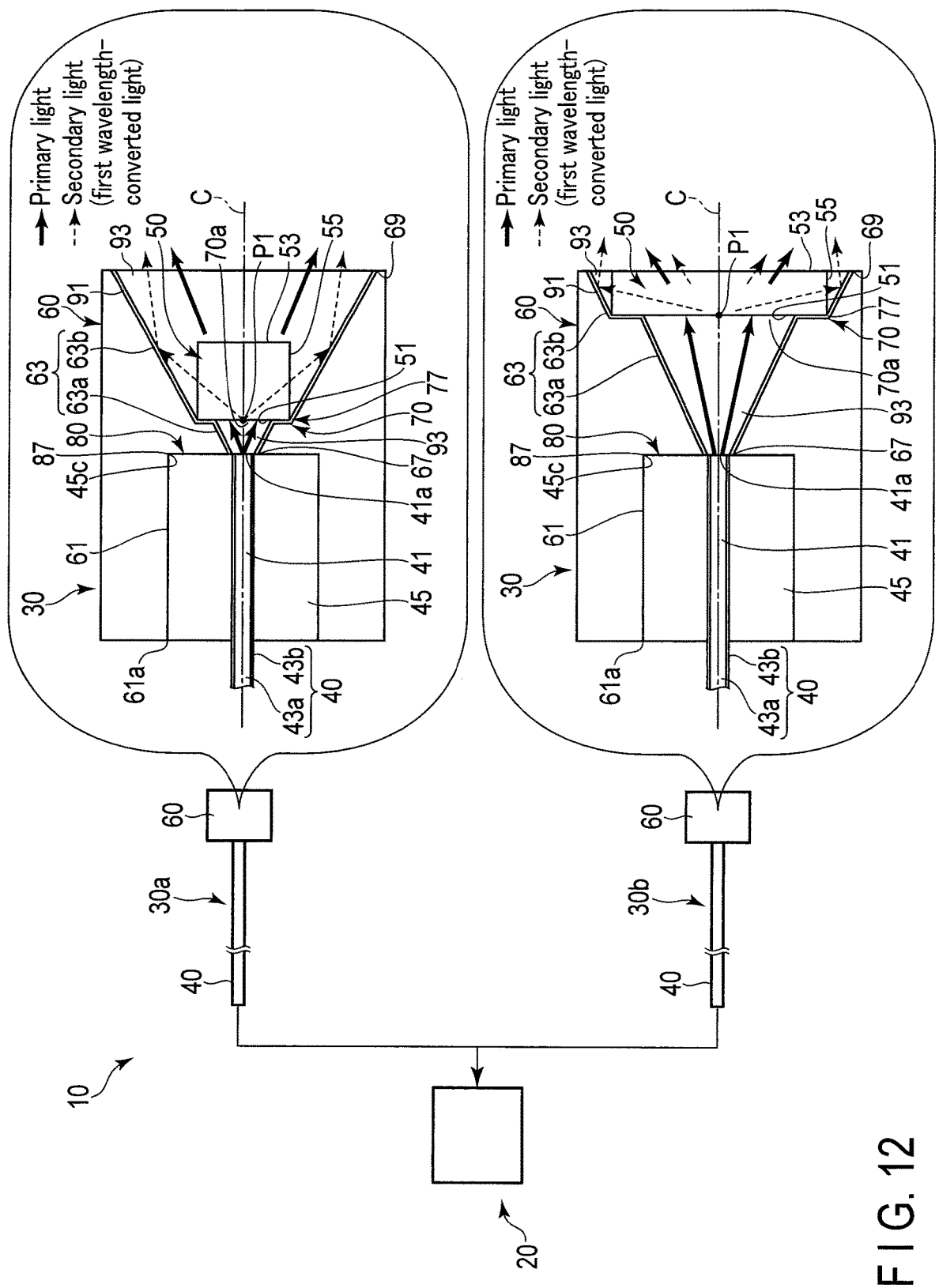
FIG. 12 is a diagram schematically showing how two illumination units having mutually different optical characteristics are optically connected to a light source unit in a replaceable manner according to the third embodiment.

The third embodiment of the present invention will be described with reference to FIG. 12. In the present embodiment, a description will be given only of the differences from the first embodiment.

In the present embodiment, illumination units 30 are used in accordance with the purposes for which illumination light is used. The purposes for which illumination light is used indicate, for example, light distribution corresponding to the angle of view of the imaging unit 280 when the endoscope 210 performs an observation operation. It is assumed that a first illumination unit 30a having a narrow distribution of secondary light used as illumination light and a second illumination unit 30b having a wide distribution of secondary light used as illumination light are used.

For example, the first illumination unit 30a is the illumination unit 30 shown in connection with the first embodiment, and the first fixing portion 70 is arranged closer to the holder entrance portion 67 than the holder exit portion 69. For example, the second illumination unit 30b is the illumination unit 30 shown in connection with modification 4 of the first embodiment, and the first fixing portion 70 is arranged closer to the holder exit portion 69 than the holder entrance portion 67. Either the first illumination unit 30a or the second illumination unit 30b is selected in accordance with the purpose of use of illumination light and is optically connected to the light source unit 20 in a replaceable manner.

In this embodiment, illumination light that is optimal for the purpose of use of the illumination light can be provided by selecting the illumination unit 30 in accordance with the purpose of use of the illumination light.

The illumination units 30 that are employed need not be limited to the first illumination unit 30a and the second illumination unit 30b. Depending on the purpose of use of the illumination light, the illumination unit 30 shown in modification 1, 2, or 3 of the first embodiment, and the illumination unit 30 shown in modification 1 of the second embodiment may be used. Although the illumination unit 30 is selected in accordance with the purpose of use of the illumination light, the present invention is not limited to this case. The illumination unit 30 may be properly selected in accordance with the purpose for which the illumination device 10 is used, the location where the illumination device 10 is arranged, and the like.

Although the illumination unit 30 is selectable, this is not restrictive. For example, each of the various types of holders 60 described in connection with the first and second embodiments and their modifications may be provided in a replaceable manner for the exit end 41 used in common to the holders 60. Each of the various types of holders 60 can be optically connected directly to the light source unit 20 and an appropriate one of them may be used for the light source unit 20.

Moreover, although the use of a single light source is assumed, this is not restrictive. For example, a first light source unit and a second light source unit may be used. The first light source unit emits blue laser light as primary light. The second light source unit emits light having a wavelength different from the wavelength of the blue laser light, for example, blue-violet laser light, as the primary light. The center wavelength of the blue-violet laser light is, for example, 405 nm.

Let it be assumed that the second light source unit is connected to the first illumination unit 30a. The blue-violet laser light emitted from the second light source unit travels through the light guide 40 and falls on the powdery first phosphor of the first light conversion member 50 of the first illumination unit 30a. Although the first phosphor well absorbs blue light having a wavelength of 445 nm and wavelength-converts the blue light to yellow fluorescence, the first phosphor hardly absorbs the blue-violet light having a wavelength of 405 nm, so that wavelength conversion hardly occurs. That is, since the first phosphor has different absorption rates for the two primary lights, the primary light with a wavelength of 445 m is well absorbed and converted into yellow fluorescence, while the primary light with a wavelength of 405 nm is hardly absorbed and is emitted as it is. However, the refractive index (e.g., approximately 1.8) of the powdery first phosphor is larger than the refractive index (e.g., approximately 1.4 to 1.5) of the first inclusion member that seals the powdery first phosphor. Therefore, the powdery first phosphor functions in substantially the same way as the first diffusing member with respect to the blue-violet laser light. That is, optical conversion is performed so that the peak wavelength and the spectrum shape are hardly converted and only the radiation angle is widened. In other words, with respect to the second light source unit, the first illumination unit 30a has the same function as the illumination unit 30 described in modification 3 of the first embodiment.

As described above, various lights can be emitted as illumination light by properly selecting combinations of the first and second light source units and the first and second illumination units 30a and 30b.

The present invention is not limited to the aforementioned embodiments, and can be reduced to practice by modifying the elements without departing from the spirit and scope of the invention. The embodiments may also be implemented by combining them as appropriate, in which case the combined advantages are obtained. Further, the aforementioned embodiments include inventions of various stages, and a variety of inventions can be derived by properly combining structural elements disclosed in connection with the embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An illumination unit comprising:
a light guide configured to guide primary light and having an exit end configured to emit the primary light;
a first light conversion member that is irradiated with the primary light emitted from the exit end and that is configured to convert at least part of the primary light into secondary light having optical characteristics different from optical characteristics of the primary light; and
a holder holding the exit end and the first light conversion member,
the holder including:
a holder entrance portion that the primary light enters;
a holder exit portion configured to emit illumination light including at least the secondary light and having a diameter larger than a diameter of the first light conversion member; and
a first fixing portion that is arranged between the holder entrance portion and the holder exit portion in a direction of a central axis of the primary light traveling from the holder entrance portion to the first light conversion member and that fixes the first light conversion member in the direction of the central axis so that the first light conversion member is arranged between the holder entrance portion and the holder exit portion,
the first fixing portion being arranged in a planar region substantially perpendicular to the central axis of the primary light and on an inner peripheral face of the holder,
the first light conversion member being in contact with at least part of the first fixing portion.

2. The illumination unit according to claim 1, wherein the first fixing portion includes a light transmission region through which the primary light traveling from the holder entrance portion to the first light conversion member is transmitted,
the first light conversion member includes a first face irradiated with the primary light, and
the first face is arranged on the first fixing portion so that the first face is away from the holder entrance portion and the first face covers the light transmission region.

3. The illumination unit according to claim 2, further comprising:
a reflection member that is arranged on at least part of the inner peripheral face of the holder and that is configured to reflect light irradiating the reflection member toward the holder exit portion, wherein
an inner diameter of the holder gradually increases from the first fixing portion toward the holder exit portion in the direction of the central axis,
the reflection member is configured to reflect the secondary light emitted from the first light conversion member and irradiating the reflection member.

4. The illumination unit according to claim 2, wherein the holder includes a first positioning portion that is arranged between the holder entrance portion and the holder exit portion in the direction of the central axis and that is configured to position the first light conversion member in a substantially perpendicular direction, substantially perpendicular to the direction of the central axis.

5. The illumination unit according to claim 4, wherein the first positioning portion is a boundary portion between the first fixing portion and the inner peripheral face, and
an outer peripheral portion of the first face is in contact with the first positioning portion.

6. The illumination unit according to claim 2, wherein the first fixing portion has a ring shape,
a diameter of the first face is smaller than an outer diameter of the first fixing portion, and
the first light conversion member has a cylindrical shape, a rectangular column shape, or a shape obtained by truncating a cone in a plane parallel to a bottom face of the cone.

7. The illumination unit according to claim 1, wherein the first light conversion member includes a first phosphor configured to wavelength-convert at least part of the primary light into the secondary light having a wavelength different from a wavelength of the primary light, and to emit the secondary light; or
the first light conversion member includes a first diffusing member configured to convert at least part of the primary light into the secondary light having a light distribution angle different from a light distribution angle of the primary light without changing the wavelength of the primary light, and to emit the secondary light.

8. The illumination unit according to claim 1, wherein the first light conversion member includes a first face irradiated with the primary light, and a second face facing the first face,
the first fixing portion is arranged closer to the holder entrance portion than the holder exit portion, and
the second face is arranged away from the holder exit portion, or arranged in a substantially identical plane to that of the holder exit portion.

9. The illumination unit according to claim 8, wherein a light distribution half-value angle of the secondary light emitted from the holder exit portion is less than 90°.

10. The illumination unit according to claim 8, wherein a light distribution half-value angle of the secondary light emitted from the holder exit portion is 90° or more.

11. The illumination unit according to claim 1, wherein the holder includes a holding hole holding the exit end directly or indirectly, an introduction port that is continuous with the holding hole and introduces the exit end into the holding hole, and a second fixing portion that fixes the exit end between the introduction port and the holder entrance portion, and
the first fixing portion and the second fixing portion are arranged substantially parallel to each other.

12. The illumination unit according to claim 11, wherein the second fixing portion is an end face arranged in a substantially identical plane to that of the holder entrance portion, and
an exit end face of the exit end and the holder entrance portion are arranged in a substantially identical plane.

13. The illumination unit according to claim 11, wherein a diameter of the second fixing portion is larger than a diameter of the first fixing portion and smaller than a diameter of the holder exit portion.

14. The illumination unit according to claim 11, wherein the holder includes a second positioning portion that is arranged on the inner peripheral face of the holder in the holding hole, is arranged between the introduction port and the holder entrance portion in the direction of the central axis, and that is configured to position the exit end in a substantially perpendicular direction, substantially perpendicular to the direction of the central axis.

15. The illumination unit according to claim 14, wherein the second positioning portion is a boundary portion between the inner peripheral face of the holder and the second fixing portion in the holding hole, and
an outer peripheral portion of the exit end is in direct or indirect contact with the second positioning portion.

16. The illumination unit according to claim 1, wherein the first light conversion member includes a first face irradiated with the primary light, and a second face facing the first face,
the holder includes a second light conversion member configured to convert at least part of the primary light into tertiary light having the optical characteristics different from the optical characteristics of the primary light and secondary light, and
the second face of the first light conversion member fixes the second light conversion member stacked on the second face.

17. The illumination unit according to claim 16, wherein the first light conversion member has a property of transmitting most of the primary light therethrough without scattering the primary light,
the second light conversion member includes a second diffusing member, and
the second diffusing member converts at least part of the primary light into the tertiary light having a light distribution angle different from a light distribution angle of the primary light without changing a wavelength of the primary light, and emits the tertiary light.

18. The illumination unit according to claim 1, wherein the holder includes a hollow portion that communicates with the holder entrance portion and the holder exit portion and in which the first light conversion member is arranged,
the hollow portion includes a rear hollow portion where the holder entrance portion is arranged, and a front hollow portion where the first light conversion member and the holder exit portion are arranged,
the rear hollow portion and the front hollow portion are arranged along the direction of the central axis, and are continuous with each other inside the holder in the direction of the central axis,
each of the rear hollow portion and the front hollow portion has a bottom face and a top face arranged in a substantially perpendicular direction, substantially perpendicular to the direction of the central axis, the top face is arranged on a side of the holder exit portion, the bottom face is arranged on a side of the holder entrance portion,
in a continuous portion between the rear hollow portion and the front hollow portion, the bottom face of the front hollow portion is continuous with the top face of the rear hollow portion and is larger than the top face of the rear hollow portion, and
the first fixing portion is arranged at the continuous portion.

19. An endoscope system comprising:
an endoscope; and
an illumination unit according to claim 1 that is located in the endoscope.

20. An illumination unit comprising:
a light guide configured to guide primary light and having an exit end configured to emit the primary light;
a first light conversion member that is irradiated with the primary light emitted from the exit end and that is configured to convert at least part of the primary light into secondary light having optical characteristics different from optical characteristics of the primary light; and
a holder holding the exit end and the first light conversion member,
the holder including:
a holder entrance portion that the primary light enters;
a holder exit portion configured to emit illumination light including at least the secondary light and having a diameter larger than a diameter of the first light conversion member; and
a first fixing portion that is arranged between the holder entrance portion and the holder exit portion in a central axis direction of the primary light traveling from the holder entrance portion to the first light conversion member and that fixes the first light conversion member in the direction of the central axis so that the first light conversion member is arranged between the holder entrance portion and the holder exit portion,
the first fixing portion being a step portion and being arranged on an inner peripheral face of the holder,
the first light conversion member being in contact with at least part of the first fixing portion.

* * * * *